US008655455B2

(12) United States Patent
Mann et al.

(10) Patent No.: US 8,655,455 B2
(45) Date of Patent: Feb. 18, 2014

(54) NEURAL STIMULATOR WITH PERCUTANEOUS CONNECTIVITY

(75) Inventors: Alfred E. Mann, Las Vegas, NV (US); Tom Xiaohai He, Santa Clarita, CA (US)

(73) Assignee: Incumed, LLC, Valencia, CA (US)

( * ) Notice: Subject to any disclaimer, the term of this patent is extended or adjusted under 35 U.S.C. 154(b) by 0 days.

(21) Appl. No.: 13/500,731

(22) PCT Filed: Sep. 30, 2010

(86) PCT No.: PCT/US2010/002658
§ 371 (c)(1),
(2), (4) Date: Apr. 20, 2012

(87) PCT Pub. No.: WO2011/046586
PCT Pub. Date: Apr. 21, 2011

(65) Prior Publication Data
US 2012/0203318 A1    Aug. 9, 2012

Related U.S. Application Data

(60) Provisional application No. 61/250,974, filed on Oct. 13, 2009.

(51) Int. Cl.
*A61N 1/00* (2006.01)
(52) U.S. Cl.
USPC .......................................... 607/116
(58) Field of Classification Search
USPC ........................ 607/116, 3; 623/32
See application file for complete search history.

(56) References Cited

U.S. PATENT DOCUMENTS

| 4,897,081 A | 1/1990 | Poirier et al. |
| 5,904,646 A | 5/1999 | Jarvik |
| 2003/0236575 A1 * | 12/2003 | Yu et al. ........................... 623/32 |
| 2004/0034392 A1 | 2/2004 | Spadgenske |
| 2005/0143781 A1 | 6/2005 | Carbunaru et al. |
| 2008/0243216 A1 * | 10/2008 | Zilberman et al. ............. 607/116 |
| 2009/0118804 A1 | 5/2009 | Moffitt et al. |

FOREIGN PATENT DOCUMENTS

| EP | 1632201 A1 | 3/2006 |
| WO | WO 92/22107 | 12/1992 |

OTHER PUBLICATIONS

PCT Int. Search Report and Written Opinion dated Dec. 2010, in related PCT App. Ser. No. PCT/US2010/002658.
EPO Extended Search Report dated Dec. 4, 2013 in related EPO App. Ser. No. 10823722.3.

* cited by examiner

*Primary Examiner* — Robert N Wieland
(74) *Attorney, Agent, or Firm* — Henricks, Slavin & Holmes LLP

(57) ABSTRACT

An implantable neurostimulation system includes both implantable and external components. Electrical connectivity between the external and implanted components is achieved through a plurality of feedthrough pins located within an insulative wall of a percutaneous port embedded in the skin. The percutaneous port has the general shape and appearance of a small thimble, embedded in the skin with its open end facing outwardly from the skin surface, and with its closed end located below the skin surface, thereby forming a cavity or dimple in the skin. Various plugs or cartridges can be removably inserted into the cavity of the percutaneous port, in various orientations, to facilitate appropriate connectivity between the external and implanted components of the system through selected ones of the feedthrough pins. A mesh edging secured around the periphery wall of the port promotes tissue ingrowth and vascularization, thereby forming a percutaneous seal around the port that prevents infection.

9 Claims, 10 Drawing Sheets

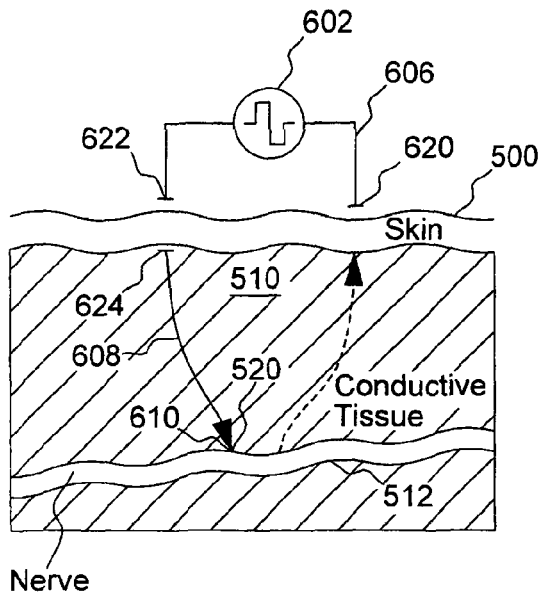
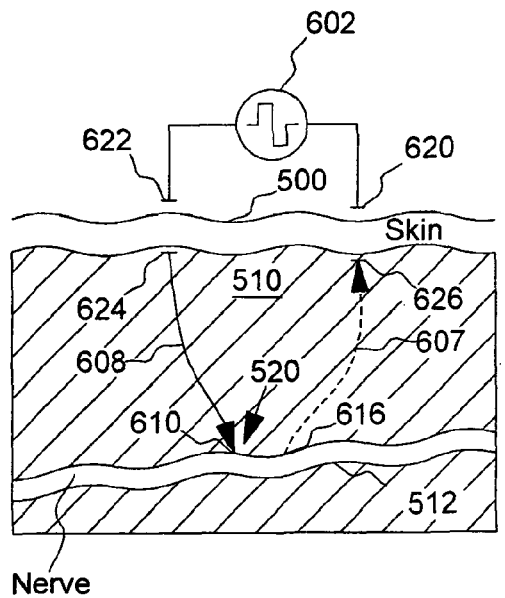
FIG. 3A  FIG. 3B
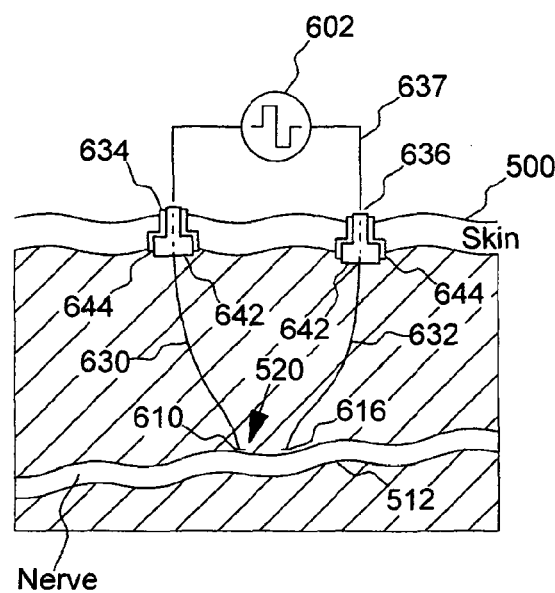
FIG. 4

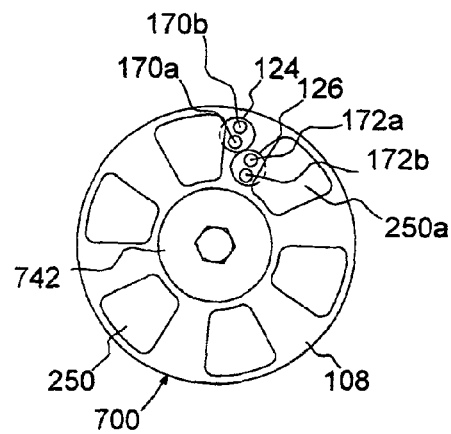
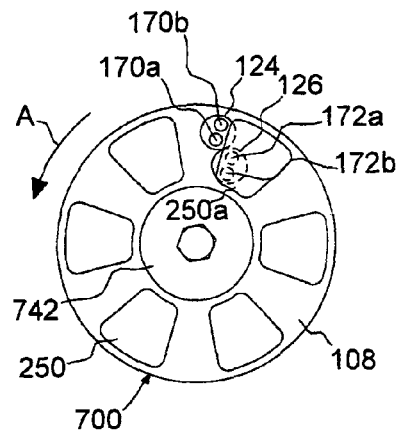
FIG. 11A  FIG. 11B
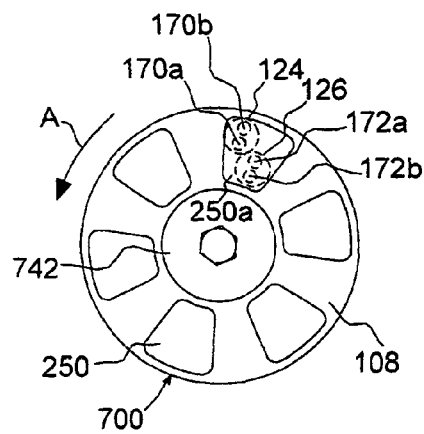
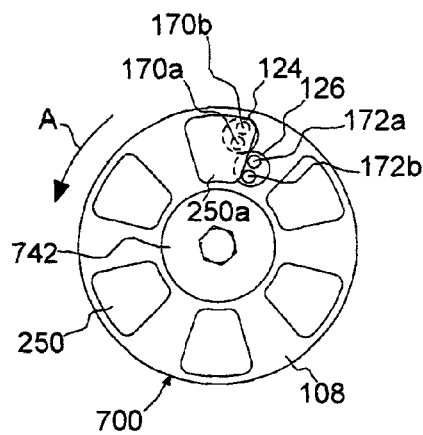
FIG. 11C  FIG. 11D
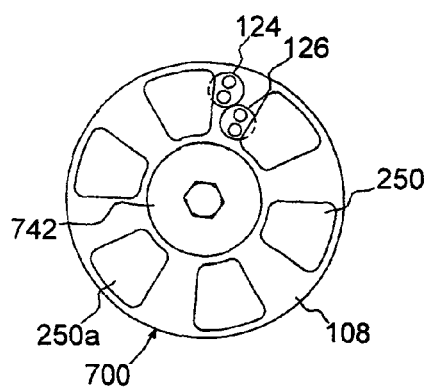
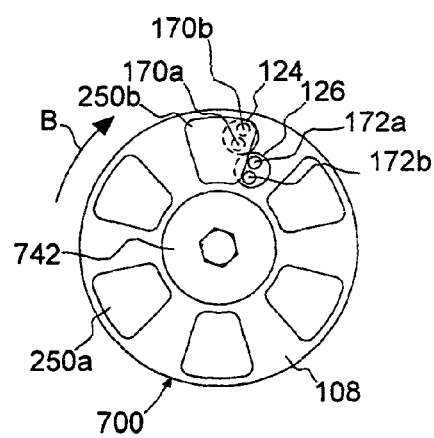
FIG. 11E  FIG. 11F

NEURAL STIMULATOR WITH PERCUTANEOUS CONNECTIVITY

RELATED APPLICATIONS

This application claims priority based on U.S. Provisional Application 61/250,974 filed Oct. 13, 2009. This application is also related to U.S. Provisional Application Ser. No. 61/224,211, entitled "Percutaneous Cochlear Implant Systems and Methods," filed Jul. 9, 2009, which application is incorporated herein by reference.

BACKGROUND

The invention relates generally to implantable medical devices or systems, and more particularly to a neural stimulator having percutaneous connectivity between implanted and external (non-implanted) components of the device or system.

A neural stimulator is an electrical stimulator that selectively applies electrical stimulation to a target stimulation site, usually a nerve, muscle or other body tissue. Neurostimulation systems have been used to provide electrical stimuli to the heart, spinal cord system, peripheral nerves, lungs, inner ear, brain, and many other body organs and tissue.

A problem that has long plagued the use of implantable medical devices is establishing reliable connectivity between implanted and external (non-implanted) portions or components of the system. Most, if not all, implantable medical devices and systems include one or more external components used with one or more implanted components. The external component(s) may be simple or complex. For example, the external component may be as simple as a permanent magnet that is placed over a magnetic reed switch located inside of the implanted device. When the magnet is placed over the magnetic reed switch, the state of the magnetic reed switch changes, which in turn may change the operating mode or state of the implanted device. Alternatively, the external component may be as complex as a programming/monitoring device that allows a user to program the implanted device to operate in accordance with a very sophisticated operating procedure.

Similarly, the implantable component(s) may be simple or complex. For example, the implanted component may be as simple as a wire or lead having an electrode at a distal end. The distal end is placed near tissue that is to be stimulated (referred to herein as "target tissue"), while the proximal end is placed near the surface of the skin, but still under the skin, where it can be coupled more efficiently to an external source of stimulation energy. Alternatively, the implanted component(s) may be as complex as a fully implantable medical device that selectively generates and applies electrical stimulation to target tissue through at least one of a large number of electrodes as a function of sensed conditions or events, and that further regularly transmits status signals to an external device to provide a status report of its operating condition.

Regardless of the complexity or simplicity of the implanted or external components of the system, there is a critical need for the implanted and external components to reliably communicate with each other at certain times during the operation of the system.

Early in the development of implantable medical devices, connectivity between the implanted and external components was achieved by simply passing a wire through the skin, with a proximal end of the wire being connected to the external device and a distal end being connected to the implanted device. (Typically, rather than having a wire or lead dangling from an incision in the skin, a connector of some type was used near the skin surface to allow easy detachable connectivity with the connector at a point near the skin surface so that only a short length of wire extended from the skin. However, the wire on the back side of the connector still passed through the skin.) Such wire provided good connectivity, but created other problems, most notably soreness and infection. As a result, a wire passing directly through the skin could never be left in place for very long without constant attention being given to keeping the hole or stoma through which the wire passed clean and disinfected.

For example, a cochlear implant system is described in U.S. Pat. No. 4,400,590 which uses wire(s) passing through the skin. However, in use, such system left an opening in the patient's skin through which infection could easily enter. Thus, because infection was a continual risk, use of a wire-through-the-skin to provide electrical connectivity between external and implanted components of a cochlear implant system of the type described in U.S. Pat. No. 4,400,590 was effectively abandoned over 25 years ago.

In order to ameliorate the disadvantages associated with a wire passing directly through the skin, other types of signal coupling links have been employed that do not require a direct signal connection through an opening made in the skin. Such links pass a signal through the skin without wires, i.e., a wireless communication. Typically, such wireless signal transfer links have included inductive coupling or radio-frequency (RF) coupling, but other types of wireless communication links are also known, e.g., optical coupling, magnetic coupling, infrared coupling, and the like.

The problem with wireless communication links, however, is that they require additional electronic circuitry on both the transmitting side and receiving side of the link. Such additional communication circuitry disadvantageously adds to the complexity, cost, size, power consumption, and efficiency of the system. Moreover, such additional communication circuitry reduces the overall reliability of the system because it inherently includes additional critical components which could fail, and in the event of such failure, shut down the system, or worse, cause the system to operate in an unsafe manner. Hence, there remains a critical need to develop smaller, simpler, more reliable, and more efficient communication links for use between the implanted and external components of an implantable medical device system.

To address this need, some have recently proposed going back to the wire-through-the-skin approach, while taking precautions to minimize the undesirable effects (soreness and infection) that normally occur when any foreign object is inserted in, or passes through, the skin. See, e.g., patent publication US 2008/0243216, published Oct. 2, 2008, entitled "System and Method For Percutaneous Delivery of Electrical Stimulation To a Target Body Tissue", hereafter the '216 Publication, which publication is incorporated herein by reference in its entirety.

In accordance with the teachings of the '216 publication, an conductive stub is embedded in the skin so as to provide an electrical pathway for electrically connecting an external component and an implanted component. At least one embodiment suggests that this stub be electrically insulated except at its distal and proximal tips. The insulation around the stub is made from a biocompatible material that has a fibrous or porous layer on its outer surface. Thus, when the stub is inserted through an incision made in the skin, tissue ingrowth into the fibrous or porous layer will occur over time thereby promoting anchorage and sealing of the epidermas around the stub. That is, a fibrin clot forms around the outer surface of the insulation that, in theory, acts as a barrier to infection, and over time becomes new skin integral with the stub. Such tissue ingrowth further serves to hold the stub in place. See, paragraphs [0089] and [0090] of the '216 Publication.

While the "stub" approach described in the '216 publication may provide a viable alternative for making a direct electrical connection through the skin when only a small number of percutaneous direct electrical connections are needed, e.g., one or two, many implantable systems used today require many more percutaneous connections than just one or two. In such situations, the "stub" approach is unsightly and unsatisfactory.

Thus, it is seen that there remains a critical need for improved connectivity between external and implanted components of a neurostimulation system. More particularly, there is a need for a percutaneous communication link that provides direct electrical connection through the skin while avoiding the problems of infection and soreness that have plagued previous through-the-skin approaches, and that also allows a sufficiently large number of independent, direct electrical connections through the skin in order to support the operation of the most sophisticated and complex medical device systems.

SUMMARY

The present invention addresses the above and other needs by providing a "percutaneous port" that may be used wherever a reliable signal communication and/or power link must be established between external and implanted components of a medical system. While a preferred embodiment of the invention to be described comprises an implanted neurostimulation system, such as a peripheral nerve stimulation system, a spinal cord stimulation system, a cochlear implant system, or any other electrical stimulation system where body tissue benefits from the selective application of electrical stimulation pulses thereto, it is to be understood that any medical system having both implanted and external components may benefit from the invention.

The percutaneous port herein described advantageously allows a large number, e.g., 3-20, or more, independent direct electrical connections to be made through the skin without creating the risk of infection that has heretofore plagued percutaneous connections. In a preferred embodiment, the percutaneous port, sometimes referred to herein as a "percuport", resembles a shallow thimble in shape, with the open, or proximal, end of the port being accessible from the outside of the skin, but with the port being inserted into the skin so only a lip of the port's proximal end extends above i.e., exteriously of the skin. The percuport shape and structure thus creates a cavity that is positioned below the surface of the skin, but which is open or accessible from outside or above the skin. As explained more fully below, selected external components or elements of the system may be removably inserted, as needed or desired, into this cavity, thus providing a great deal of flexibility in how such implantable medical system is configured and used. (As used herein, the term or phrase "removably inserted", or similar language, means that an item may be placed in a first position, such as inside of the cavity of the percuport, and then later removed therefrom, e.g., later being extracted or pulled from the cavity of the percuport. This process of "insertion" and subsequent "removal" can occur over and over, as many times as is needed or desired, without harm or damage to the components being thus "removably inserted.")

Porous, e.g., mesh material is bonded to the exterior surface of the percuport's cavity, where "exterior in this context means all or most all of the surfaces of the percuport except those on the inside of the cavity. This porous or mesh material may be made from a fine mesh material, e.g., a titanium mesh, as described more fully hereinafter. Because titanium is compatible with body tissue, tissue ingrowth occurs in the mesh. This is the desired consequence because such ingrowth effectively anchors the percuport in place and seals the mesh with new-grown skin and vascularized tissue, resulting in a percutaneous seal around the percuport that blocks bacterial and/or viral infections from entering the body adjacent the percutaneous port. The percutaneous port thus becomes an integral part of the skin once this tissue ingrowth into the mesh occurs, with the open cavity of the percuport becoming, as it were, a dimple or indentation in the skin.

A bottom or distal end of the percuport, e.g., a bottom surface of the cavity created by the percuport, is made, at least partially, from a non-conductive plate or sheet material. That is, this non-conductive plate or sheet is made from a material that acts as an electrical insulator, such as a ceramic or some types of polymers. Typically, a multiplicity (three or more) of feedthrough pins extend through this insulative sheet or plate. Such feedthrough pins are not limited to extending through the bottom or distal end of the percuport, but can also extend through the walls of the percuport, as a particular design or application may dictate. These feedthrough pins (sometime referred to herein as "feedthrus"), strategically postioned in the percuport's side and/or bottom surfaces, allow direct electrical connection to be established between the implanted and non-implanted (i.e., external) components of the system.

The implantable medical systems utilizing the percutaneous connectivity provided by the inventions described herein may take on a wide variety of configurations and applications. Some systems, for example, may include all external (non-implanted) circuitry and components with only leads and electrodes being implanted. Other systems may include all, or mostly all, implanted circuitry and components, including a rechargeable power source, with only programming, diagnostic and/or recharging components being external. Still other systems may include some implanted components, such as pulse generator circuitry, a multiplexer or switch, leads and electrodes, and some external components, such as a power source, a control unit, and diagnostic and programming units.

One embodiment of a percuport system made in accordance with the teachings presented herein comprises a peripheral nerve stimulation system that includes implanted leads and electrodes and an external (non-implanted) stimulator circuit. The stimulator circuit is connected to a selected set of leads and electrodes so as to provide a desired stimulation pulse to an electrode(s) using a desired stimulation mode (e.g., monopolar or bipolar stimulation) at a desired target tissue location. In one variation of this embodiment, the particular leads/electrodes that provide the stimulation may be manually selected by the user of the system through rotation or positioning of a plug or cartridge that is inserted into the percuport cavity. In another variation of this embodiment, the particular leads/electrodes that provide the stimulation may be electronically selected by including an implanted multiplexer circuit inserted in series with the distal end of the percuport feedthrus and the implanted leads/electrodes.

Another embodiment of a percuport system made in accordance with the teachings provided herein comprises a fully implantable neurostimulation system that includes an implantable rechargeable battery and an hermetically-sealed housing wherein electrical neurostimulator circuits reside. The implantable battery may reside in the same housing wherein the neurostimulator circuits reside, or in a separate housing flexibly connected to the neural stimulator circuits. A percutaneous port advantageously provides direct through-the-skin connectivity with the battery and neurostimulation circuits. Hence, when recharging the battery, or reprogramming the neurostimulation circuits, external units that perform the recharging or programming function may connect directly with the implanted battery and/or neurostimulation circuits through a cable having a plug at its distal end configured to be removably inserted into the percuport cavity.

In one variation of this fully implantable embodiment, during normal operation (i.e., when not recharging or reprogramming), a cover plug (which does not have a cable or wires connected to it) is inserted into the percuport cavity. Rotation of the cover plug relative to the percuport cavity allows a user of the percuport system to manually control some basic functions associated with operation of the neural stimulator system, such as on/off, electrode selection, stimulation magnitude, and the like.

In accordance with another variation of this fully implantable embodiment, a plug having a wireless receiver embedded therein, such as a Bluetooth® receiver, receives control signals from a remote control unit and sends such signals through the percuport to the implanted stimulator circuits. This allows the user, through use of the remote control, to control some basic functions of the percuport system, such as on/off, electrode selection, stimulation magnitude, and the like.

Advantageously, the percutaneous connectivity provided as described herein provides a high degree of flexibility in how a system using a percutaneous port (i.e., a "percuport system") may be configured and optimally used to best meet the needs and wants of a particular patient or a particular application. That is, numerous configurations or embodiments of a percuport system allow different combinations of components of the system to be either permanently implanted or not implanted, as needed, to suit the needs of a particular design or application. The non-implantable components can be readily replaced or removed, as needed, and replaced with new, upgraded or recharged components.

In operation and use, implantable components of the percuport system may attach or be connected to the implanted, or distal, side of the feedthrus, while non-implantable components of the percuport system, e.g., a battery (in some embodiments), or test/programming cables, may connect to the non-implanted, or proximal, side of the feedthrus. Some of the non-implantable components may be sized to fit within the percuport cavity so as to make necessary contact with the proximal side of the feedthrus located on the inside surfaces of the percuport cavity.

It is a feature of the systems herein described to provide a neurostimulation system wherein some components of the system are implanted and some components of the system are non-implanted, and wherein the required electrical or signal links between the implanted components and non-implanted components are made through a percutaneous port embedded in the skin of a user of the system.

It is another feature of the systems herein described to provide a neurostimulation system that is at least partially implanted and that does not require radio frequency telemetry nor inductive coupling to provide a communicative link for power and/or data signals that must be transferred between the implanted portions of the system and the non-implanted portions of the system.

If is still a further feature of the neurostimulation system described herein to provide electrical connectivity between implanted and non-implanted components through a percutaneous port, and wherein the percutaneous port is configured to allow tissue ingrowth and vascularization, which tissue ingrowth and vascularization provides a percutaneous seal around the periphery of the perctaneous port that functions as a very effective barrier to infection.

Yet another feature of the systems herein described is to provide a modular-based implant system wherein different component groupings or modules provide different embodiments suited for different applications or needs. In one embodiment or configuration, for example, most components of the system may be implanted and only a few components of the system (such as a programming/testing module and recharging module) are non-implanted. In another embodiment or configuration, most components of the system may be non-implanted and only a few components of the system (such as an electrode lead) are implanted. In this manner, a full spectrum of possible embodiments and configurations of the implant system—ranging from a system that is almost fully implanted to a system that is mostly non-implanted—may be designed and fabricated in order to best meet the needs and demands of a particular patient group or application.

As an additional feature of the systems herein described, in accordance with one aspect thereof, an implant system having implantable and non-implantable components electrically coupled together through a percutaneous port allows existing, approved and fully tested implantable components to be used in implantable modules or housings, and existing, approved and tested non-implantable components to be used in non-implantable modules, housings or configurations, to thereby shorten the time required to obtain regulatory approval for the implant system as a whole.

BRIEF DESCRIPTION OF THE DRAWINGS

The above and other aspects, features and advantages of the present invention will be more apparent from the following more particular description thereof, presented in conjunction with the accompanying drawings. These drawings illustrate various embodiments of the principles described herein and are a part of the specification. The illustrated embodiments are merely examples and do not limit the scope of the disclosure.

FIG. 3A schematically depicts a monopolar peripheral nerve stimulation system as shown in FIG. 2A, but wherein the through-the-skin connection to the implanted electrode at or near the target tissue location is eliminated and replaced with a capacitive, or non-direct contact, type of coupling between a surface electrode and a subcutaneous electrode.

FIG. 3B schematically depicts a bipolar peripheral nerve stimulation system as shown in FIG. 2B, but wherein the through-the-skin connections that connect the pair of implanted electrodes at or near the target tissue are eliminated and replaced with capacitive, or non-direct contact, coupling between surface electrodes and subcutaneous electrodes.

FIG. 4 schematically illustrates a bipolar peripheral nerve stimulation system using two "stub" through-the-skin connectors that allow direct, electrical connection between the external pulse generator and the implanted electrodes.

FIGS. 11A-11F are plan views showing a plurality of sensible members moving relative to a pair of sensors contained within a bottom edge of a percutaneous port, wherein being able to sense the location of the sensible members provides a manual user interface that allows a user the ability to generate control signals for controlling at least some functions of an implantable neurostimulation system through manual rotation of a plug or cartridge inserted into the percutaneous port.

Throughout the drawings, identical reference numbers used in different drawings represent functionally equivalent elements, but not necessarily identical elements.

DETAILED DESCRIPTION

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
  I. Introduction and Overview
  II. Exemplary Percutaneous Port
  III. Exemplary Neurostimulation Systems utilizing a Percutaneous Port
  IV. Exemplary Manual Control Methodologies
  V. Conclusion The section titles and overall organization of the present detailed description are for the purpose of convenience only and are not intended to limit the present inventions.

I. INTRODUCTION AND OVERVIEW

Figure 1:
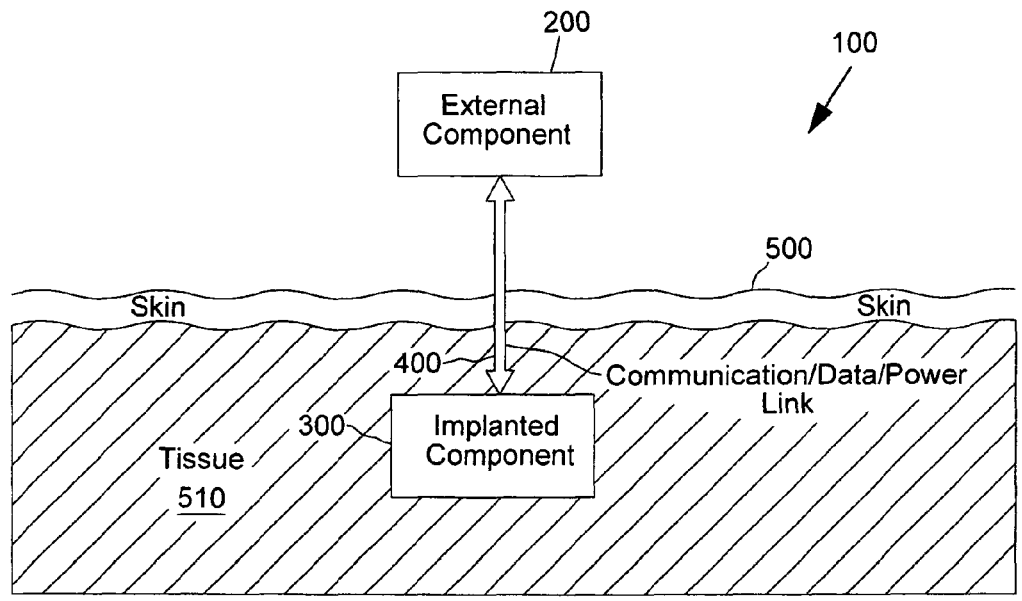
FIG. 1 schematically illustrates an implantable medical system having both external (non-implanted) components and implanted components, and wherein a communication link is established between the external and implanted components in order to allow data, power or other signals to be passed between the external and implanted components.

FIG. 1 schematically illustrates an implantable medical system 100 having both external (non-implanted) components 200 and implanted components 300, and wherein a communication link 400 is established between the external and implanted components in order to allow data, power or other signals to be passed between the external and implanted components. As shown in FIG. 1, the implanted components 300 are placed or "implanted" so as to reside beneath or under the skin layer 500 of a patient. As such, the implanted components are surrounded by living tissue 510.

As is known in the art, living tissue is made up of and includes many ingredients and substances, all of which in combination provide a very harsh environment in which to place anything that is to last or survive. Materials that can survive in living tissue, and which are compatible with the harsh environment provided by living tissue, are said to be "biocompatible". Biocompatible materials are also not harmful to the living tissue, i.e., do not dissolve or infuse harmful substances into the living tissue that could cause the tissue, or living organs that are fluidly coupled to the living tissue, to become severely damaged, or to cause a cancer to develop, or to die. Thus, when foreign materials are placed or implanted in living tissue, it is critically important that the materials be biocompatible, not only to assure the survival of the materials thus implanted, but also to protect the living tissue, and its surrounding organs, from being damaged.

Living tissue has electrical properties very similar to a saline solution. For purposes of the present inventions, that means the tissue is conductive, and electrical current can readily flow therethrough as guided by different voltage potentials. As is well known in the art, electrical current always flows from a point of a first voltage potential to a point of a second voltage potential, where the first and second voltage potentials differ, i.e., are not the same. The amount of current that flows between the first and second points is a function of the difference between the first and second voltage potentials. The resistance that exists between the two points as current flows between them can be expressed as V=IR (an expression known as Ohm's Law), where "V" represents the voltage potential difference between the two points between which the current flows, "I" is the current, and "R" is the resistance. What this means for directing current flow in living tissue is that a current path must be provided to the target tissue location that offers a much lower resistance path to flowing current than does the surrounding tissue. As is known in the art, such current path(s) can be provided by implanting wires, or leads, made from biocompatible materials. A typical implantable lead includes a conductive core, made from a biocompatible conductive metal, surrounded by an insulative sheath made from a biocompatible, non-conductive material, such as silicone or some polymers.

Thus, still with reference to FIG. 1, it is seen that the implanted components 300, as well as those portions of the communication link 400 that reside under the skin layer 500, must either be made from a biocompatible material, or placed in a housing made from a biocompatible material, e.g., such as titanium or stainless steel, in order to survive the harsh environment created by living tissue.

Those portions of the communication link 400 that are implanted may be made from an implantable lead, as described above. Alternatively, wireless communication links can also be employed, as is known in the art.

Those portions of the implanted components 300 that comprise electrical circuitry, on the other hand, are typically not made from biocompatible materials. Moreover, electrical circuits, made from, e.g., capacitors, resistors, transistors, integrated circuits, and the like, cannot function properly when connected as an electrical circuit when the electrical circuit is immersed in a saline solution, without some type of protective barrier that coats or surrounds them to shield them from the conductive and harmful properties of living tissue. Thus, when the implanted components 300 include electrical circuitry, such circuitry must be housed in a suitable biocompatible housing. Further, such biocompatible housing must be hermetically sealed to prevent fluids associated with the surrounding living tissue from leaking inside the housing and causing the electrical circuitry to stop working. Any electrical contact with the circuitry inside of the hermetically sealed implantable housing must occur through an electrical feedthrough pin that passes through a wall of the hermetically sealed housing. Herein, such feedthrough pin may also be referred to as just a "feedthrough" (and sometimes spelled simply as "feedthru").

An electrical feedthrough is typically made by a conductive pin having exposed distal and proximal ends to which electrical contact can be made, but with the body of the pin being embedded and sealed in a ceramic or other suitable insulator. The insulator is also hermetically sealed around its periphery to the wall(s) of the housing in which the electrical circuitry is housed. Thus sealed, when a housing having feedthrough pins is implanted in living tissue, no fluid path exists through or around the feedthrough pin through which body fluids can flow or enter the inside of the housing. Thus, the circuitry inside the housing is protected from harmful body fluids so that it can perform its proper function. Moreover, the living tissue that surrounds the housing is likewise protected from the non-biocompatible materials found in the components of the electrical circuitry.

Figure 2A:
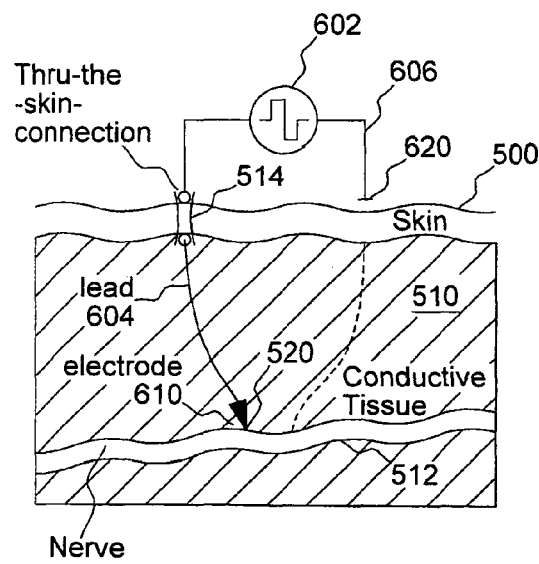
FIG. 2A schematically illustrates a peripheral nerve stimulation system wherein an external pulse generator provides monopolar stimulation to a target tissue location by passing a wire through-the-skin to an electrode located at or near the target tissue location, and wherein a return path for the stimulation signal is provided through conductive tissue back to the skin surface where a return electrode is located.

Referring next to FIG. 2A, a simple neurostimulation system 600 is schematically illustrated. The system includes a pulse generator 602 that selectively generates and provides an electrical stimulation pulse that is delivered to a desired target tissue location 520 near or on a nerve 512. As shown, the pulse generator 602 is an external (non-implanted) pulse generator, and the type of stimulation provided is "monopolar" stimulation. Monopolar stimulation occurs when the stimulation pulse is delivered to the target tissue location 520 through a single wire or lead 604 connected to an electrode 610 located at or near the desired target tissue location 520. A return path for the current associated with the stimulation pulse occurs through the conductive body tissue 510 to a location on the skin 500 where a reference electrode 620 is located. The reference electrode 620, in turn, is connected to the pulse generator through a suitable external wire or lead 606. Thus, monopolar stimulation occurs through a single electrode 610 located at or near the target tissue stimulation site 520, with a return path for the stimulation current being provided through the tissue. The electrode 610 is connected or coupled to the stimulation source, the pulse generator 602, through a single wire or lead 604. The advantage of monopolar stimulation is that it only requires one implantable electrode at the target simulation site, and hence only one implantable wire or lead that connects to the electrode.

As shown in FIG. 2A, the single wire or lead 604 that connects the pulse generator 604 to the implanted stimulating electrode 610 passes through the skin 500 by way of a through-the-skin connection point 514. Such connection point 514 has heretofore been simply a hole or tunnel made through the skin 500 through which the wire or lead 604 passes. Such through-the-skin connection functions suitably for only a short period of time, and must be continually monitored for cleanliness to prevent infection. Through-the-skin connections made by tunneling a passage way through the skin in order to allow a wire or lead 604 to connect an external component (e.g., the pulse generator 602) to an implanted component (e.g., the electrode 610) are undesirable for most purposes.

Figure 2B:
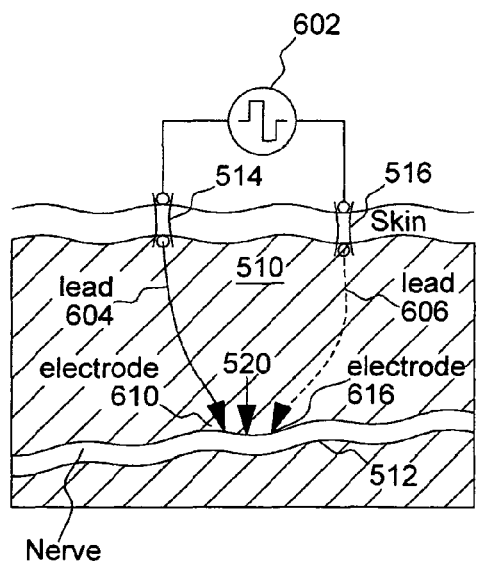
FIG. 2B schematically illustrates a peripheral nerve stimulation system as shown in FIG. 2A, but wherein the electrical stimulation of the target tissue location is achieved using bipolar stimulation achieved by passing two wires through-the-skin that are connected to respective electrodes at or near the desired target tissue location.

FIG. 2B schematically illustrates a peripheral nerve stimulation system as shown in FIG. 2A, but the electrical stimulation of the target tissue location 520 is achieved using "bipolar" stimulation. Bipolar stimulation is achieved by passing two wires or leads through-the-skin, each of which is connected to respective electrodes at or near the desired target tissue location 520. A first lead 604 connects the pulse generator 602 to a first electrode 610 located at or near the target stimulation site 520. A second lead 606 connects the return path of the pulse generator 602 to a second electrode 616 located in close proximity to the first electrode 610. Bipolar stimulation offers the advantage of allowing stimulation to be more focused at the desired tissue target site 520, and can often achieve desired results using a stimulation pulse of less energy or amplitude than is required for monopolar stimulation. Bipolar stimulation has the disadvantage of requiring an additional implanted lead and electrode, which adds to the complexity of the implantation process and to the system.

For the configuration shown in FIG. 2B, the bipolar stimulation system requires two through-the-skin connection points 514 and 516. The disadvantages and undesirability of through-the-skin connection points have already been described.

Turning next to FIG. 3A, there is schematically illustrated a simple monopolar peripheral nerve stimulation system, similar to that shown and described in connection with FIG. 2A, but wherein the undesirable through-the-skin connection 514 (which connects to the implanted electrode at or near the target tissue location) is eliminated and replaced with a capacitive, or non-direct contact, type of coupling between a surface electrode 622 and a subcutaneous electrode 624. Such through-the-skin coupling avoids the problems, described above, of having to maintain a hole or tunnel made in the skin through which a lead or wire can pass. Rather, the skin 500 is left intact so that it can provide its intended function for protecting the tissue underneath it, yet a stimulation signal (generated by the pulse generator 602) can be coupled from the surface electrode 622 to the subcutaneous electrode 624, and then be directed by a fully implanted lead 608 to the stimulation electrode 610 implanted at the stimulation target site 520. As is characteristic of monopolar stimulation, the return signal associated with a stimulation pulse directed to the electrode 624 as thus described passes through conductive tissue 510 and is coupled with a return electrode 620. For the configuration shown in FIG. 3A, the return electrode 620 is located on the surface of the skin 500. The return electrode 620 is connected to the pulse generator 602 via external lead 606.

FIG. 3B schematically depicts a bipolar peripheral nerve stimulation system similar to that shown in FIG. 2B, described above. However, unlike the configuration shown in FIG. 2B, where undesirable through-the-skin connections 514 and 516 provide a hole or tunnel through the skin to allow lead wires 604 and 606 to pass therethrough, the system of FIG. 3B does not pass any wires through the skin. Rather, the system shown in FIG. 3B utilizes capacitive, or non-direct contact, electrode pairs for each current path, to couple the stimulation current pulse through the skin 500. That is, one surface electrode 622 couples with one subcutaneous electrode 624. A stimulation pulse applied to surface electrode 622 is coupled to subcutaneous electrode 624. This coupling allows the stimulation pulse to pass along implantable lead 608 to distal electrode 610, where the stimulation pulse is applied to the tissue 510 at or near the desired target site 520. A return path for this stimulation pulse is provided through nearby electrode 616, which conducts the return stimulation current through implanted lead 607 to subcutaneous electrode 626. Subcutaneous electrode 626 then couples this return stimulation current through the skin 500 to surface electrode 620, and surface electrode 620 passes the current back to the signal generator 602. In this manner, the desired target stimulation site 520 may be stimulated in bipolar fashion with the paired electrodes 610 and 616 without having to have a wire or lead passing through the skin. The non-invasive bipolar stimulation scheme shown in FIG. 3B thus advantageously avoids the problems attendant with the use of open through-the-skin passageways, as are used with the stimulation scheme shown in FIG. 2B.

Representative peripheral nerve stimulation systems that utilize configurations similar to those shown in FIGS. 3A and 3B, and which generally avoid direct through-the-skin connectivity links, as are used in the configurations of FIGS. 2A and 2B, are described more fully in Gaunt et al., "Method of Routing Electrical Current to Bodily Tissues Via Implanted Passive Conductors", U.S. Pat. No. 7,502,652; Glukhovsky et al., "System for Transmitting Electrical Current to a Bodily Tissue", US Patent Publication US 2009/0054952 A1; and Glukhovsky et al., "Improvements to an Implant System and Method Using Implanted Passive Conductors for Routing Electrical Current", WIPO Publication WO 2007/002741 A1. This patent (U.S. Pat. No. 7,502,652) and these patent publications (US 2009/0054952 A1 and WIPO WO 2007/002741 A1) are incorporated herein by reference.

The systems of the type shown in FIGS. 3A and 3B, where direct electrical connectivity through the skin via a lead wire passing through a hole formed in the skin is avoided, function adequately for many applications. However, for other applications, it may still be advantageous to have an implantable stimulation system where the connectivity between the external components and the implanted components can be realized through a direct electrical connection. The biggest advantage of direct electrical connection through the skin is simplicity. With simplicity comes reduced size and cost, fewer components, higher reliability, and lower power consumption. In short, but for the problems (e.g., infection, discomfort) associated with having to pass a wire or other conductor through an opening in the skin, the direct-electrical-connection approach of the systems described in connection with FIGS. 2A and 2B would generally be preferable.

Recognizing this potential advantage, a way of conducting an electrical signal directly through the skin without having to leave an open hole or wound in the skin through which a wire or lead can pass has recently been proposed. See, e.g., Zilberman et al., US Patent Publication US 2008/0243216 A1, which publication is incorporated herein by reference. Zilberman et al. teach, among other things, the use of a "stub" type of terminal that can be embedded in the skin. The stub terminal includes a center conductive post, or element, surrounded, at least in some embodiments, by a coating of insulative material. When embedded in the skin, one end of the conductive post extends above the skin, and the other end of the conductive post extends below the skin. The insulative material insulates the conductive post from the surrounding conductive tissue. Thus, a current flowing through the conductive post is confined to flowing through the conductive post, and does not flow through tissue surrounding the conductive post in the area immediately around the stub terminal. Instead, the current can be directed to wherever the lead or wire attached to the ends of the stub direct it. The surrounding insulative material is configured to encourage ingrowth of tissue. Such tissue ingrowth, over time, heals the skin so that the stub terminal eventually becomes like it is part of the skin, and prevents infection from entering the skin at the stub terminal location.

FIG. 4 schematically illustrates a bipolar peripheral nerve stimulation system of the type described previously in connection with FIG. 2B, but wherein two "stub" terminals, of the type described in the Zilberman publication, US 2008/0243216 A1, are used to provide the electrical connectivity through the skin, rather than having a lead wire(s) pass through the skin. Thus, as seen in FIG. 4, connection between an external pulse generator 602 and a pair of implanted electrodes 610 and 616, positioned at or near the desired target stimulation site 520, is achieved through the use of two stub terminals 634 and 636 that are embedded in the skin. Each stub terminal has a center conductive post 642 having a proximal end and a distal end. In this context, the "proximal" end is the end of the post that extends above the skin, and the "distal" end is the end of the post that extends below the skin. (In other contexts, e.g., when describing an implantable lead, the "proximal" end of the lead is that end closest to the signal source, and the "distal" end of the lead is the end of the lead farthest away form the signal source, and is usually the end where a terminating electrode is placed. The "distal" end of the lead, with its accompanying electrode, is thus often placed at or near the desired target stimulation site.)

As further seen in FIG. 4, an external lead or wire 635 connects one side of an external pulse generator 602 with the proximal end of the stub terminal 634. An implantable lead 630 connects the distal end of the stub terminal 634 to a first stimulating electrode 610 located at or near the target tissue stimulation location. A second stimulating electrode 616, paired with the electrode 610 for bipolar stimulation, is connected to the distal end of the second stub terminal 636 via implantable lead 632. The proximal end of the stub terminal 636 is connected to the other side of the pulse generator 602. With this configuration, bipolar stimulation of the target tissue location 620 can readily be achieved via direct electrical connectively between the stimulating electrodes 610 and 616, yet without having to have an open hole in the skin through which the wires connecting the generator 602 to the electrodes 610 and 616 must pass.

The stimulation systems illustrated thus far in connection with FIGS. 2A, 2B, 3A, 3B and 4 have been greatly simplified. In reality, stimulation systems may utilize numerous configurations in order to be used for numerous applications. In order to better accommodate such various configurations and applications, what is needed is a way to provide direct electrical connectivity through the skin for a multiplicity of separate, independent electrical connections. In order to address this need, the inventions disclosed herein incorporate a percutaneous port, or "percuport", as part of the stimulation system.

II. EXEMPLARY PERCUTANEOUS PORT

As used herein, the term "percutaneous port" (or "percuport", for short, or sometimes just "port") refers to a means for making electrical and/or signal connection through the skin of a patient, e.g., from an external component or device to an implanted device or component, or vice versa, without the need for transmitting an RF signal or using inductive coupling schemes. In its simplest form, one could argue that a "percutaneous port" is simply a wire that passes through the skin. However, a wire that just passes through the skin would not function for purposes of the present disclosed subject matter because infection would occur within a short time, and the wire would have to be removed. Hence, a "percutaneous port" of the type used with the systems described herein not only must provide the direct electrical or signal connection that a wire, or wires, passing through the skin would provide, but it must do so in a way that greatly minimizes or eliminates the risk of infection. An exemplary percutaneous port of the type that may be used with the invention(s) described herein is more fully described in applicant's copending U.S. patent application Ser. No. 12/390,425, filed Feb. 21, 2009, entitled "Partially Implantable Medical Devices and Methods", which application is incorporated herein by reference.

As already mentioned, an exemplary percutaneous port made in accordance with the teachings of the inventions described herein, advantageously provides direct electrical connectivity through the skin for numerous connections, typically 3-20 independent connections, or more. Moreover, such connectivity is achieved in a relatively small surface area of the skin and in a way that is non-obtrusive and aesthetically pleasing. For many applications, a wired cable connects through the percuport to implanted components only for programming, recharging or diagnostic purposes. Hence, during normal operation of the neurostimulation system, i.e., after programming, recharging or testing, there are no wires or cables at all that need to be connected to the percuport, During these times (when not programming, recharging or testing) the percuport can be hidden with a cover that is flush with the skin.

Figure 5:
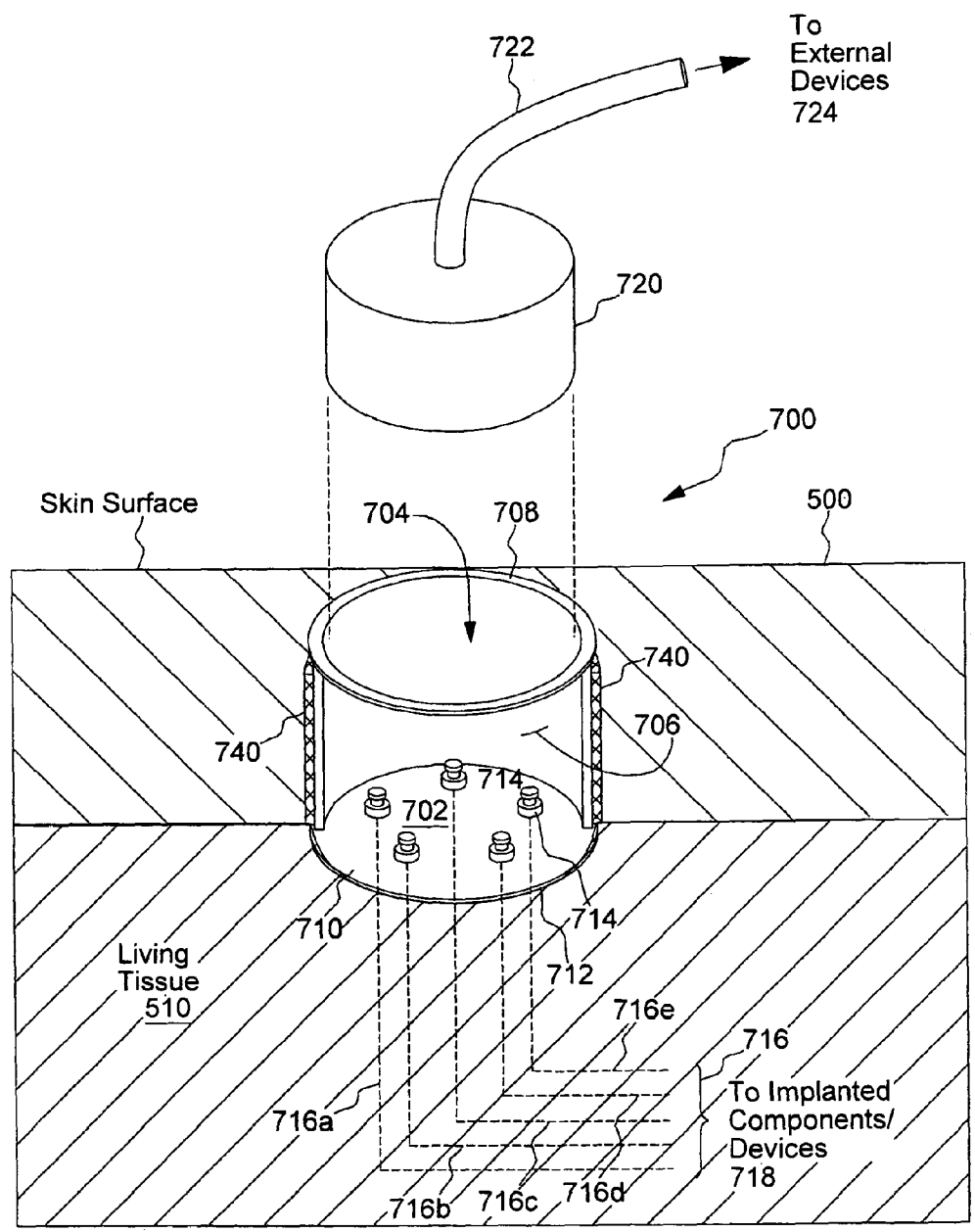
FIG. 5 schematically illustrates a percutaneous port, or "percuport", that allows multiple through-the-skin electrical connections to be established while at the same time minimizing the risk of infection and soreness.

FIG. 5 schematically illustrates one embodiment of a percutaneous port 700, or "percuport", made in accordance with one preferred embodiment of the inventions described herein. The percuport advantageously allows multiple through-the-skin electrical connections to be established while at the same time minimizing the risk of infection and soreness. The schematic illustration of the percutaneous port 700 in FIG. 5 shows five separate connections that can be made through the percuport in order to interconnect external devices or equipment with implanted components or devices. This number of connections is only exemplary. As few as one connection, and as many as 20 or more connections may be provided depending upon the particular type of neurostimulation system, or other medical system, that uses the percuport. In most instances, and for most applications, at least three or four independent connections will be provided through the percuport.

The percutaneous port 700 shown in FIG. 5 includes an insulative plate 702 located at the bottom of a cavity 704. The cavity 704 is formed by a cylindrical or tubular side wall 706 in combination with the bottom insulative plate 702. An upper edge 708 of the cylindrical side wall forms a rim. When the percuport 700 is embedded on or in the skin 500 of living tissue 510, the rim 708 is typically positioned so that the rim is flush with, or extends slightly above, e.g., 1 to 3 mm above, the surface of the skin 500. Most of the volume of the cavity 704, however, resides below the surface of the skin, thereby having the cavity 704 appear as a dimple or indentation in the skin.

The insulative plate 702 located at the bottom of the cavity 704, for the embodiment shown in FIG. 5, has a first surface 710 that faces upward (as the cavity is oriented in FIG. 5) towards the open end of the cavity 704 where the skin surface is located. A second surface 712 of the insulative plate 702 is exposed to tissue 510 below and around the cavity 704. Thus, when embedded in the skin, the wall(s) 706 and bottom insulative plate 702 of the Percuport 700 serve the same basic function as the skin 500—they provide a protective barrier or layer that protects the living tissue 510 under the skin from exposure to the external environment.

Still with reference to FIG. 5, it is seen that a plurality of feedthrough pins 714 extend through the insulative plate 702. Five such feedthrough pins 714 are shown in FIG. 5, but this number is only exemplary. Typically, as has been previously indicated, for most applications with which the percuport is used, at least three or four feedthrough pins will be used, but as many as twenty, or more, could also be employed, depending on the particular application. A percuport could be fabricated with only one feedthrough pin 714, but if only one electrical connection through the skin was all that were needed, a plurality of feedthrough pins would still likely be employed so that the pins could be electrically connected in parallel to provide redundancy and thereby improve reliability.

Each feedthrough pin 714 is made from a biocompatible conductive material, such as a biocompatible metal, that allows an electrical current to flow through it with little or no resistance, and thus allows an electrical connection to be established between a proximal end of the pin (the end extending out or accessible from the first surface 710 of the plate 702) and a distal end of the pin (the end extending out or accessible from the second surface 712 of the plate 702, which second surface is exposed to the body tissue 510 below the skin, and is the surface on the underneath side of the plate 702 as drawn in FIG. 5).

It should be noted that the insulative plate 702 need not necessarily comprise the entire bottom surface of the cavity 704 as shown in FIG. 5, All that is required is that the insulative surface comprise a portion of the bottom surface, or of the wall surface, where the feedthrough pins are placed. Because the insulative plate 702 is typically made from some sort of ceramic material, or other material that has electrical insulative properties, how much of the bottom surface (or of a wall surface) that is made from the ceramic or other insulative material will be determined in large part by how the percuport is assembled during manufacture. Numerous manufacturing techniques could be used to assemble the percuport, and to include therein an appropriate surface area through which the feedthrough pins could be placed. For purposes of this patent application, and the inventions described herein, any of these known, or yet to be developed, manufacturing techniques could be used to manufacture and assemble the percutaneous port 700.

The distal end of each feedthrough pin 714 is connected to a respective lead 716. Five such leads, 716a, 716b, 716c, 716d and 716e, are shown in FIG. 5 with a proximal end of each lead being attached to the distal end of the one of the five feedthrough pins 714. The number five is only exemplary, and any number of leads may be used depending upon how many feedthrough pins 714 are needed for a particular neurostimulator system application. A distal end of each lead 716a, 716b, 716c, 716d and 716e is then directed through tissue 510 to appropriate or designated implanted components/devices 718 (not shown in FIG. 5). Sometimes the devices or components to which the distal end of the implanted leads are attached will be as simple as an electrode that is positioned near target tissue that is to be stimulated. Other times the devices may be complex implantable neurostimulator circuits or devices, or power sources for such devices, or sensors used with such devices, as dictated by the particular application with which the neurostimulator system is used.

An external plug or cartridge 720 is configured to be inserted into the cavity 704 of the percuport 700 in order to facilitate electrical connection with the proximal ends of the feedthrough pins 714. For many applications, a cable 722 is connected to this plug 720. The cable may have a plurality of wires or conductors in it, e.g., five wires or conductors, and each wire or conductor is terminated inside of the plug 720 at a respective terminal so that when the plug 720 is inserted all the way into the cavity 704, each terminal makes contact with the proximal end of a respective feedthrough pin 714. Thus, by removably inserting the plug 720 into the cavity 704 of the percuport 700, it is possible to have individual wires within the cable 722 establish electrical connectivity with the respective implanted leads 716a, 716b, 716c, 716d and/or 716e, via the feedthrough pins 714. In this manner, electrical connectivity can be established through the percutaneous port 700 between external devices 722 (that are connected to a proximal end of the cable 722) and implanted devices 718 (that are connected to a distal end of the leads 716).

Still with reference to FIG. 5, a mesh material 740 is disposed around a periphery of the insulative plate 702 or tubular wall 706. This mesh material, for the configuration shown in FIG. 5, is attached to the cylindrical wall 706 that engages with the periphery of the insulative plate 702. This mesh material 740 is made from a biocompatible material and is configured to promote tissue ingrowth and vascularization. More details concerning this mesh material are described below and/or in the references cited herein that are incorporated herein by reference.

As thus described, it is seen that through use of the percutaneous port 700, an external part, e.g., the plug. 720, or an external device 724 connected through a cable to the plug 720, is able to establish connectivity with a proximal end of at least one of the feedthrough pins 714 located in the cavity 704 of the percutaneous port 700 when the plug is removably inserted into the percutaneous port 700. When this connectivity occurs between the external device 724 and the proximal end of a feedthrough pin 714 located in the cavity of the percuport 700, connectivity is also established with the distal end of the feedthrough pin 714, which also establishes direct connectivity with an implanted part 718 via a lead 716 attached to a distal end of the feedthrough pin 714. Hence, use of the percuport 700 advantageously establishes electrical connectivity between the external part and the implanted part of the percutaneous implant system through direct electrical connection through the feedthrough pins passing through the insulative plate of the percutaneous port.

Figure 6:
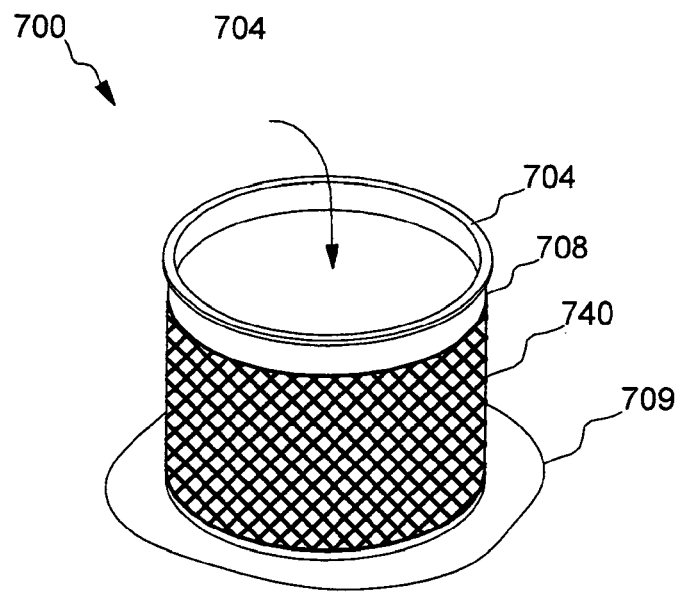
FIG. 6 shows one embodiment of a percuport made in accordance with the teachings presented herein, prior to embedding the percuport in the skin of a user.
Figure 7:
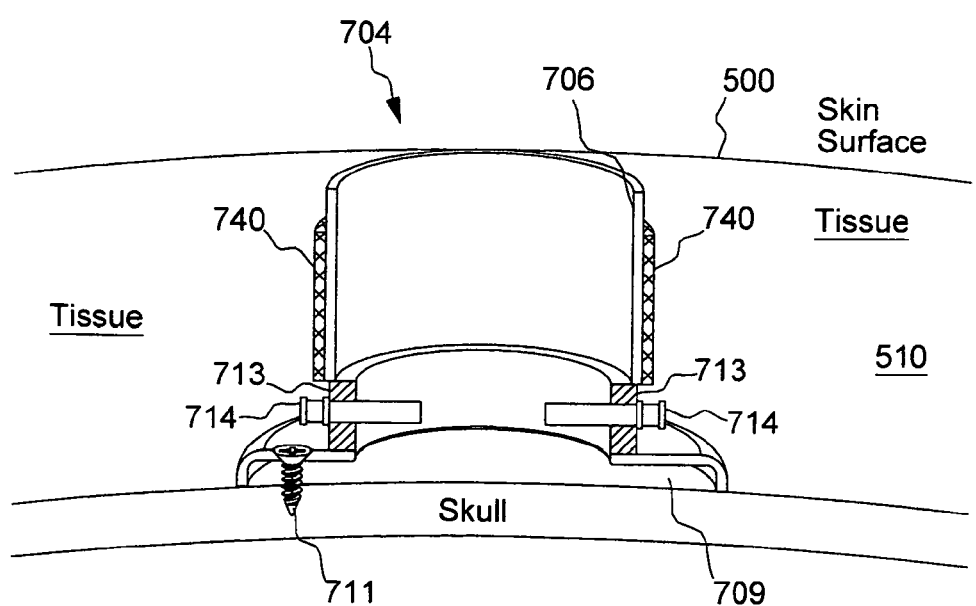
FIG. 7 shows a cross-sectional view of one embodiment of a percuport made in accordance with the teachings presented herein wherein a bottom edge of the percuport is adapted to be placed against and secured to a bone surface.

Turning next to FIGS. 6 and 7, there is shown another embodiment of a percuport 700 made in accordance with the teachings presented herein. The percuport 700 shown in FIG. 6 shows the percuport prior to being embedded in the skin of a user. The configuration shown in FIG. 6 is particularly well suited for situations where its lower surface rests against the surface of a bone, or other hard tissue, such as the skull. Placing the bottom surface of the percuport against the skull is something that is may be needed, e.g., when the percuport is used as part of a cochlear implant system, a middle ear implant system, or deep brain stimulation system.

FIG. 6 shows a perspective view of an exemplary percuport 700 which is merely illustrative of the many different types of ports that may be used in connection with the systems and methods described herein. FIG. 7 shows a sectional view of the port 700 when embedded in skin tissue so that its base resides against the skull of a patient.

An exemplary implant location of percutaneous port 700, when used, e.g., in a cochlear implant system, or a deep brain stimulation system, is on the head of a user, as described more fully, e.g., in Applicant's copending application, Ser. No. 61/224,211, filed Jul. 9, 2009, entitled "Percutaneous Cochlear Implant Systems and Methods", which application is also incorporated herein by reference. Typically, when used in a cochlear implant system, the port 700 will be located a certain distance behind the ear (e.g., 2-3 cm) and behind the hair line. Such an implant location is advantageous for many reasons. For example, because port 404 is located behind the hairline, it is generally not visible or noticeable to others because it is just a small circle near the skin surface, much like a mole or scab. In some examples, this circle may be colored or otherwise disguised.

The exemplary port 700 shown in FIGS. 6 and 7 is circular in cross-section in order to accommodate one or more circular components. It should be noted, however, that percutaneous port 700 may have cross-sectional shapes other than circular in order to, for example, accommodate components that are oval, square, rectangular, or otherwise shaped.

Percutaneous port 700 may have any suitable length as may serve a particular patient or application. In some examples, the length of port 700 may be slightly more than the thickness of the skin. If mounted on the surface of a bone, e.g., on the skull, a pocket having a depth of a few millimeters may be made in the skull (or other bone surface), or a spacer can be added in order to accommodate a port 700 having a depth greater than the depth of the skin above the skull. In some examples, a proximal end of port 700 may extend beyond the skin when implanted by up to 2 or 3 mm. Alternatively, the proximal end of port 700 may be substantially flush with the surface of the skin. Hence, an exemplary length of port 700 may be 12 to 14 mm. In other patients (e.g., children) with skin that is less thick (e.g., 5 mm), the length of port 700 may be reduced accordingly. For example, the length of port 700 may be 6 to 7 mm for such patients. Likewise, the diameter of port 404 may vary as may serve a particular patient. It will be recognized that these measurements, and all others presented herein and in the drawings, are merely illustrative and are not to be construed as limiting in any way.

As shown in FIG. 6 and/or 7, port 700 may include a tubular or cylindrical wall 706 with a rounded rim 708, a layer of porous material 740 surrounding wall 706, and a base flange 709. Rounded rim 504, which may be located adjacent to the epidermal surface when port 700 is implanted into the patient, strengthens tubular wall 706 and eliminates what might otherwise be a sharp edge that could be uncomfortable to the touch. Tubular wall 706 defines a tubular or cylindrically shaped lumen or cavity 704 in which one or more external components of a percutaneous neorostimulation system 100 may be housed and/or through which one or more components may be accessed and/or controlled. (As previously mentioned, the cavity 704 may be made to have cross-sectional shapes other than tubular or cylindrical, e.g., oval, rectangular, square, or triangular, although any corners associated with polygonal shapes are typically rounded sufficiently to avoid sharp or uncomfortable edges). Tubular wall 706 may be made out of any suitable biocompatible material (e.g., titanium, nitinol, stainless steel, gold, or platinum) as may serve a particular application.

In some embodiments, a center protrusion may extend up from the bottom or floor of the port 700 to accommodate rotation or keyed-positioning of components that are inserted into the cavity 704 of the port 700.

The layer of porous material 740, which may at a minimum be located just below the patient's epidermis and in contact with the dermis, is configured to encourage tissue ingrowth and vascularization so as to create an infection resistant barrier, or percutaneous seal, around tubular or cylindrical wall 706 after implantation. The layer of porous material 740 extends around the entire circumference of tubular wall 706 (as shown) and may extend from one longitudinal end of tubular wall 706 to the other, or over only a portion of tubular wall 706. In certain exemplary implementations, the layer of porous material 740 may include a mesh of intersecting fibers of any suitable biocompatible material, such as a biocompatible metal (e.g., titanium, nitinol, stainless steel, gold, or platinum) or a biocompatible polymeric material (e.g., polyolefins, Teflon, nylon, Dacron, or silicone). The mesh is formed by cross-winding the fibers in multiple layers to define a porosity conducive to promoting tissue ingrowth (e.g., pore sizes within a range of 50 to 200 microns and having a porosity of 60 to 95%). The infection resistant barrier may be enhanced by incorporating antimicrobial and/or anti-inflammatory constituents into or beyond the layer of porous material 740. Additional details concerning such porous material layers may be found in U.S. Patent Pub. Nos. 2004/0204686, 2007/0112334 and 2007/0149949, each of which is incorporated herein by reference.

Base flange 709 may be configured to facilitate fixation of port 700 to the skull or other bone or hard tissue surface. To this end, one or more screws 711, or other affixation devices, may be used to affix base flange 709 of port 700 to the skull or other hard tissue surface. In some alternative embodiments, port 700 is not affixed to the skull and instead simply floats with the tissue ingrowth that forms into porous material 740 to secure port 700 within the tissue.

As shown in FIG. 7, a feedthrough plate 713 is disposed in a portion of wall 706 near a distal end of cavity 704, but not at the distal end of cavity 704. For the configuration shown in FIG. 7, where base flange 709 presupposes that the distal end of port 700 will reside against a hard surface, such as the skull, the feedthrough pins 714 may extend out through the side wall 706, thereby avoiding the hard bone tissue of the skull or other hard surface. Thus, the feedthrough plate 713 is positioned above the distal end of cavity 704 so that the distal end of the feedthrough pins 714 reside above the surface of the skull, thereby facilitating attaching leads thereto without compromising the integrity of the skull.

Thus, it is seen that in combination the tubular wall 706, the distal end or bottom of port 700, and the feedthrough plate 604 (which comprises a portion of the wall 706) define a receiving region or cavity 704 into which one or more components may be inserted. In some embodiments, as shown in FIG. 5, feedthrough plate 710 comprises a bottom surface of port 700. In other embodiments, as shown in FIG. 7, feedthrough plate 713 comprises a portion of tubular wall 706. In yet other embodiments, as shown in Applicant's copending patent application Ser. No. 61/224,211, the feedthrough plate may comprise a wall of an hermetic chamber built into the bottom of port 700.

Feedthrough plate 710 or 713 may assume various shapes and forms. Whatever the shape or form, however, the function of the plate is essentially the same: to provide a surface through which feedthrough pins 714 may extend in order to provide electrical connectivity between one side of the plate with the other. This is necessary because one side of the plate defines a region or surface area that is appropriately sealed or protected from the surrounding environment, while the other side of the plate is not. Electrical circuitry that is implanted, for example, must typically reside in an hermetically sealed cavity or otherwise be sealed and protected from body fluids and tissue if it is to reliably perform its intended function over a long period of time.

III. EXEMPLARY NEUROSTIMULATION SYSTEMS UTILIZING A PERCUTANEOUS PORT

Figure 8:
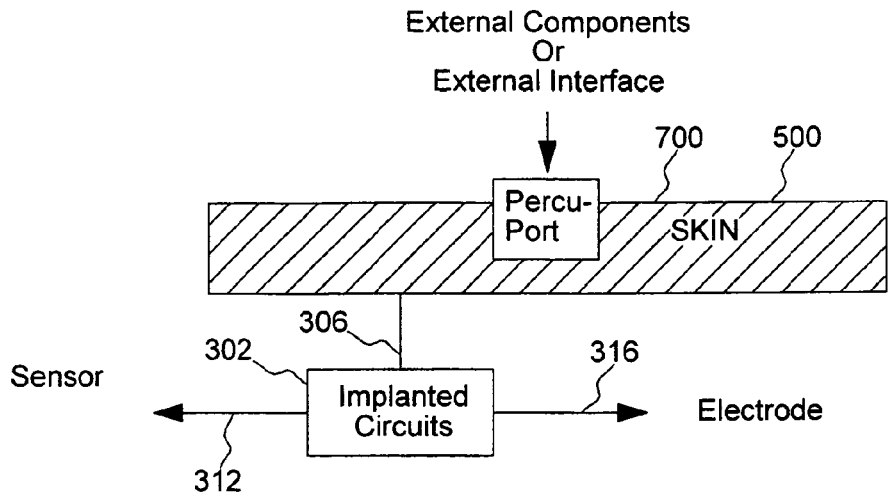
FIG. 8 schematically depicts the manner in which a percutaneous port may be used with the systems and methods described herein to provide a link between external and implanted components of an implanted neurostimulation system.

FIG. 8 schematically depicts the manner in which a percutaneous port may be used with the systems and methods described herein to provide a link between external and implanted components of an implanted neurostimulation system. As FIG. 8 depicts, a percutaneous port 700 is found in all embodiments of the systems and methods described herein relating to a percutaneous nerostimulation system. Thus, as seen in FIG. 8, every such system includes a percuport 700 that is embedded in the skin 500 of a patient. Below the skin, or "implanted" in the patient, are implanted circuits 302 that carry out the functions of the system. These functions are the same as are carried out in any implant system. The circuits 302 may have implantable leads 312 and 316 extending therefrom that connect respectively to a suitable sensor or a lead with electrodes. The circuits in housing 302 are connected to the percuport 700 via a suitable connection 306, which may be a flexible cable or other suitable implantable cable or lead. Alternatively, in some embodiments, the percuport 700 may be affixed to the top or side of the circuitry housing 302, in which case feedthrough pins 314 (see FIG. 5) may extend all the way through a bottom insulative plate 702 of the port 700 into the inside of the housing 302.

The particular electronic circuitry housed in the implanted circuits 302, including any particular modules of a particular configuration, along with its manner of operation, programming codes, stimulation levels and/or stimulation patterns, and the like, will not be described in detail in this patent application, if at all. This is because such details are generally not the subject of the present application and the invention(s) described and claimed herein. Rather, the invention(s) described and claimed herein focus more on the manner in which the particular modules used by or within a particular configuration of a neurostimulation system can be configured or arranged relative to a percutaneous port 700. Thus, it is seen that a percutaneous port 700 is a common feature of all of these configurations.

The actual circuitry used within the various modules associated with the configurations of the neurostimulation systems of the present invention(s), as well as the assembly and manufacturing techniques used to make the implantable housings, leads, connectors and electrodes associated with these configurations, may be of any suitable design, whether presently existing or yet to be developed. In fact, that is one of the potential advantages of the present invention (in some configurations): by using circuits and components that already exist, and that have been tried and tested and approved for use in medical implantable devices, the percutaneous neurostimulation implant system(s) described herein may be brought to market much quicker than could otherwise occur.

Of course, as with any new configuration, some changes or revisions in existing designs and circuits need to be made in order to have all the modules, circuits and components of the invention interface and cooperate together for the system to function correctly and efficiently. Where such changes are more than routine, and not readily discernable by a person of skill in the art given the descriptions and explanations already provided herein, or provided in the documents that are incorporated herein by reference, such will be described, as necessary, with sufficient detail to allow a person of skill in the art to make and practice those revisions and changes.

Figure 9:
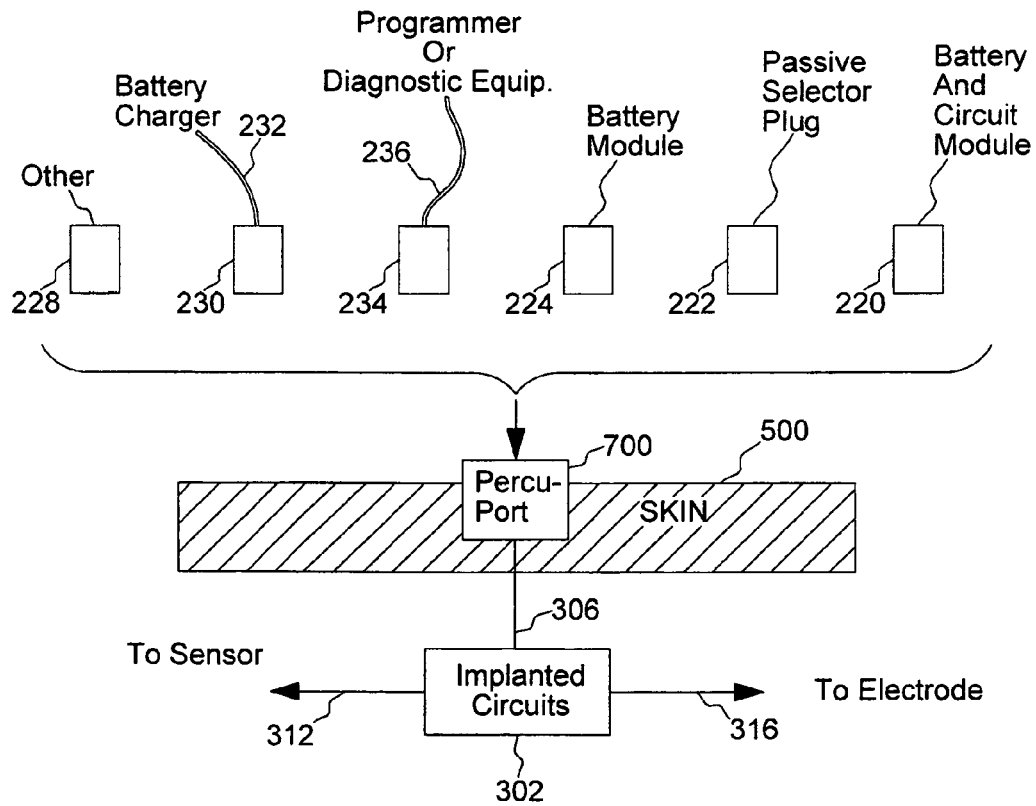
FIG. 9 schematically depicts, in an exploded view, exemplary components of an implanted neurostimulation system, or elements used with an implanted neurostimulation system, that may reside external to the percutaneous port, any one of which may be selectively removably inserted into the percutaneous port in order to provide a desired function.

As seen in FIG. 8, various elements or components of a stimulation system are external to the patient, i.e., not implanted under the skin. Yet, these external components or elements must interface with the implanted circuits 302. The purpose of the percutaneous port 700 is to allow this interface or connectivity to occur, regardless of the form the external components may take. FIG. 9, for example, shows, in an exploded view, exemplary external devices and components that may interface with the implanted circuits 302. The particular external devices and components which are used depend on the particular application and system design that is used for the implanted circuits 312.

For example, one external component that may interface with the implanted circuits 302 through the percuport 700 is a battery/circuit module 220. Such module includes a battery, which provides operating power for both the implanted and external components of the system. Such module may also include, as needed, at least some additional circuitry, e.g., power management and monitoring circuitry, used with the neurostimulation system. While FIG. 9 shows the battery and circuit module 220 as one module, it is to be understood that these components could be realized in separate modules or components that are placed, e.g., piggy-back into the percuport 700. That is, a power management module could be inserted into the most distal end of the percuport 700, and then a battery, e.g., a disc battery, could be inserted in the proximal end of the percuport so as to reside on top of the power management module. The advantage of having both the battery and power management module circuits located or housed in the percuport 700 is that they can be readily replaced and upgraded, or recharged, as needed.

Alternatively, if the implanted circuits 302 include all of the circuitry necessary to carry out the functions of the neurostimulation system, but do not include a battery, then a battery module 224, which in its simplest form is just a battery, e.g., a disc battery, may be all that is needed to be inserted into the percuport 704.

Other modules, represented by the generic box 228 in FIG. 9, may also be fabricated for insertion into the percuport 700 in order to add functionality to the neurostimulation system. Module 228, for example, could be an FM receiver adapted to receive a FM control or informational signal that, once received within the module 228, could be sent to the implanted circuits 302, thereby enabling the user of the system to remotely send, e.g., control or informational signals to the implanted circuits 302.

In a similar manner, module 228 could be a Bluetooth® receiver that enables reception of signals that are transmitted to or from a mobile phone or other device that utilizes Bluetooth® technology. Alternatively, module 228 could include a flash memory that stores prerecorded signals, such as MP3 files, that when inserted into the percuport 700 allows the user to use such prerecorded signals in a beneficial manner.

Another component that could be inserted into the percuport 700, in accordance with some embodiments of the neuron stimulator systems described herein, is a passive selector plug 222. In this context, the term "passive" simply means that in this embodiment, there is no electronic circuitry included within the selector plug 222. Rather, the passive plug functions as a stopper, like a cork, that is inserted into the cavity of the percuport 700. Unlike a cork, however, the plug is adapted for rotational movement within the cavity 704 of the percuport 700, and includes some sensible elements, e.g., conductive metal contacts or traces, spaced around its distal end or sides in a desired pattern. Because of this rotational movement, and the pattern of conductive traces or contacts included on at least one surface thereof, this passive selector plug may also be referred to herein as a "cartridge".

The passive selector plug 222 will be described in more detail hereinafter. Essentially, however, the passive selector plug 222, when inserted into the port 700, allows the user, by manually rotating the plug in prescribed directions (clockwise, counterclockwise), and prescribed distances or magnitudes (¼ turn, ⅓ turn, ½ turn, etc.) to manually control some functions of the implanted neurostimulation system, such as on/off, amplitude of a stimulus pulse, selection of an electrode(s) where a stimulus pulse is to be applied, and the like.

For many embodiments of an implanted neurostimulation system, there is a recurring need to access the implanted circuits 302 for the purpose of charging the battery (if a rechargeable battery is included in the implanted circuits 302) and for programming the circuits or performing diagnostic tests on the circuits. Battery charging is readily achieved by simply inserting a battery charger plug 230 into the cavity of the percuport 700. Such battery charger plug 230 is connected to a cable 232 that in turn connects to an appropriate external battery charger circuit. Alternatively the battery charger can be a small module that includes a battery that is connected to a plug that fits into the percuport 700. Also, an auxiliary battery can be inserted into the percuport 700 to extend the operating time of a system with an implanted rechargeable battery.

Programming is similarly achieved by inserting a programming plug 234 into the percutaneous port 700. A cable 236 attached to the plug 234 allows the implanted circuits 302, via the connectivity provided by the percuport 700, to be connected directly to external programming or diagnostic equipment. Such external programming or diagnostic equipment is typically realized through using custom software loaded on a laptop or other suitable computer, as is known in the art.

Thus, it is seen that the neurostimulation system shown in FIGS. 8 and 9 allows a wide variety of configurations and embodiments to be realized. The percutaneous port 700 is the common element that makes all of these configurations and embodiments possible.

Figure 13:
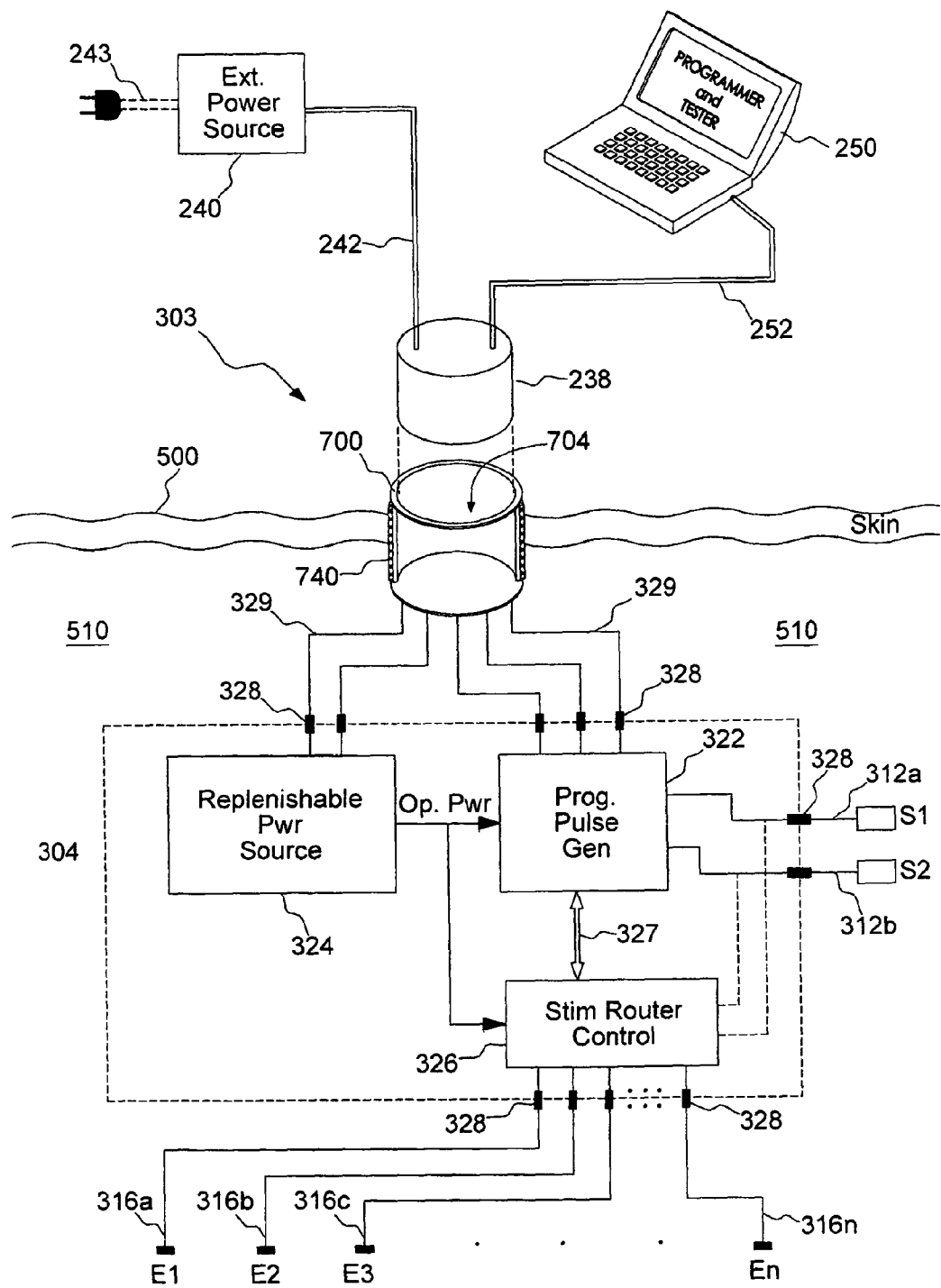
FIG. 13 schematically depicts a multi-channel implantable neurostimulation system that uses a percutaneous port to selectively establish power connectively between an external power source and an implanted power source (for recharging or replenishing the implanted power source), and to also selectively establish signal/data connectivity between an external programmer/diagnostic device and an implantable programmable pulse generator and an implantable stimulation router control module.

Turning next to FIG. 13, there is shown a schematic representation of a fully implantable, programmable, multi-channel neurostimulation system 303. A key component of the system 303 is the percutaneous port 700. Use of the port 700 advantageously allows a user of the system 303 to selectively establish direct electrical connectivity between external components and implanted components. The external components used with the system 303 typically include an external power source 240 and an external programming/diagnostic device 250. The implanted components used with the system typically include an implanted replenishable power source 324, such as a rechargeable battery, a programmable implantable pulse generator 322 and an implantable stimulation router circuit 326.

Control circuitry for controlling the operation of the implantable circuits may be included within the programmable pulse generator circuits 322, the stimulation router circuits 326, or both. Such control circuitry includes the necessary processing circuitry, memory circuitry, switching circuitry, and the like, used to cause stimulation pulses to be generated at appropriate times and with desired pulse amplitudes and pulse widths, and delivered to desired target tissue locations, as programmed by the external programming device 250. An appropriate signal/data bus 327 connects the programmable pulse generator circuits 322 with the stimulation router circuits 326

The external power source 240 may comprise a recharging circuit connected to conventional source of power, such as a 110 VAC socket located in a user's residence (connected through a power cord 243), which voltage is then isolated, e.g., through a transformer, and converted to a lower AC voltage, and then rectified and converted to the desired dc voltage level. Alternatively, the external power source 240 may comprise a conventional battery, or some other suitable source of power. The external power source 240 connects with the implanted power source via a power cable 242 that is coupled to a suitable plug 238 adapted to be removably inserted into the cavity 704 of the percuport 700. Such external power source is typically used only to recharge or replenish the implantable power source 324. Thus, so long as the implanted power source 324 has sufficient energy stored therein to power the operation of the system 303, the external power source is not needed and need not be connected to the system 303 through the percutaneous port 700.

The external programming device 250 may comprise a conventional laptop or notebook computer loaded with appropriate programming software. It may connect with the implanted programmable pulse generator 322 and/or stimulation router circuits 326 via a USB cable 252, or similar cable, that also connects to the plug 238, which plug 328 is adapted to be removably inserted into the cavity 704. Once the implanted circuits have been programmed, there is no need to keep the programming device 250 connected to the implanted circuits, unless testing or monitoring of the implanted circuits is desired.

For the discussion that follows relative to FIG. 13, it is assumed that all of the implanted components reside in the same hermetically sealed implantable housing 304, and that electrical connection with the circuits and components housed within the implantable housing is established through the use of feedthrough pins 328 that are mounted in the housing walls at appropriate locations. (A proximal end of these feedthrough pins 328 is connected to the distal end of feedthrough pins 714 [see FIG. 5] of percuport 700 via a suitable implantable wire 329. A proximal end of the perpuport feedthrough pins 714 makes electrical contact with respective terminals of the plug 238 when such plug is removably inserted into the cavity 704 of the percuport 700, as previously described.) Thus, as seen in FIG. 13, in order to establish electrical connectivity between the implanted circuits and the external circuits through the percuport 700, implanted wires 329 interconnect the distal end of the feedthrough pins 714 located in the bottom (or other location) of the percuport 700 with a proximal end of feedthrough pins 328 mounted on one of the surfaces of the implantable housing 304. In some embodiments, one or more of the implanted components 324, 322, and 326 may reside in a separate hermetically-sealed implantable housing that is electrically coupled with the other implantable components through appropriate implanted leads or insulated wires that interconnect the implanted housings through feedthrough pins mounted on the respective housings.

Use of a percuport 700 with the system 303 shown in FIG. 13 allows direct power connectively to be selectively established between an external power source 240 and an implanted power source 324. Such direct connectivity allows the implanted power source 324 to be recharged or replenished, when needed, without having to inductively couple power into the system. Hence, power transmission, reception, rectification and regulating circuits that have traditionally been used within an implanted device to receive power from an external device through the use of, e.g., an implanted coil inductively coupled with an external coil, and all the associated circuitry used therewith to generate and transmit a carrier signal, rectify the received signal, filter it, and then regulate power voltages are not needed. Being able to eliminate these types of power circuits from the implanted circuitry greatly simplifies the system 303 and reduces its cost, and improves its reliability.

Further, still with reference to FIG. 13, the percutaneous port 700 used with the system 303 also allows direct signal connectivity to be selectively established between the implanted circuit portions of the neurostimulation system 303 and the external programmer/diagnostic device 250. Thus, the wireless transmission schemes, with their modulated-data-signal-superimposed-on-a-carrier transmission signal, that have heretofore been used to provide such signal and data connectivity between external and implanted devices need not be employed. This means that much, if not all, of the circuitry needed to support and carry out such signal transmission schemes is not needed, thereby again greatly simplifying the system 303, reducing its cost, and making it more reliable.

The implantable, programmable neurostimulation system 303 shown in FIG. 13 may be used for a wide variety of applications where a stimulation signal or pulse needs to be routed to different tissue locations in a controlled manner. Such system 303 employs multiple electrodes E1, E2, E3, . . . En, where n may be as low as two, and as high as 20 or more, depending on the application involved. Each electrode E1, E2, E3, . . . En is connected to a stimulation router control module 326 via respective implanted insulated wires 316a, 316b, 316c, . . . 316n. Feedthrough pins 328 allow these leads to interconnect with the stimulation router control circuitry 326 located in the hermetically sealed housing 304. Typically several, if not all, of these wires 316a, 316b, 316c, . . . 316n may be included in the same lead wire bundle or cable.

In operation, stimulation pulses may be directed to multiple electrodes E1, E2, E3, . . . En at the same time. Further, different groupings of the electrodes E1, E2, E3 . . . En may also operate as separate stimulation channels. Hence, the system 303 may be programmed to function as a multichannel neurostimualtion system by programming different regimes of stimulation pulses to be generated and directed to different groups of electrodes at the same or different times.

The stimulation router control circuitry 326 receives the stimulation signal or pulse from the programmable pulse generator 322. In operation, the pulse generator and stimulation router circuits, in combination, may be as simple as a single current source connected to a multiplexer circuit, or as complicated as a bank of programmable, bidirectional current sources connected to each electrode wire, wherein each current source can be selectively turned on or off so as to provide current stimuli of any desired amplitude, pulse width and polarity on any selected electrode at any selected time.

The programmable pulse generator 322 (or the stimulation router control circuitry 326) may also have at least one sensor S1 connected to it through an insulated wire 312a via a feedthrough pin 328. For many applications, a second sensor S2, connected to the programmable pulse generator 322 (or to the router control circuitry 326) by way of insulated wire 312b and a different feedthrough pin 328, may also be employed to compliment sensor S1. The sensors S1 and/or S2 may simply be an electrode positioned to sense potentials or voltages at selected tissue locations. Alternatively, the sensors S1 and/or S2 may comprise implantable sensors adapted to sense, e.g., body temperature, blood $SO_2$ levels, blood sugar levels, tissue movement, or the like. In some embodiments, one or more of the sensors S1 or S2, or additional sensors, may be mounted inside of the hermetically-sealed housing 304, in order to sense events or other operating data that occur during the operation the system.

As has been indicated, the programmable pulse generator 322 generates stimulation pulses in accordance with a regime that has been pre-programmed into its circuitry. Such regime may be automatically altered or adjusted, as needed, as a function of parameters sensed through the sensors S1 and/or S2. Further, parameters sensed through sensors S1 and/or S2 may be sent through direct signal connections established through the percuport 700 to the external programmer/tester device 250. These parameters may be sent to the programmer/tester 250 either in real time (if the programmer/tester is connected through the percuport 700 at the time of transmission), or they may be stored in the programmable pulse generator in a suitable memory device and uploaded to the programmer/tester 250 at a later time when a connection is established through the percuport 250.

Operational data associated with the operation of the implanted neurostimulation system 303 may likewise be transferred to the external programmer/tester device 250. Such operational data may include the amount of charge left in the implantable power source 324, impedances measured at each electrode, internal temperature of the implantable pulse generator, data stored in the memory of the implantable pulse generator, and the like. By monitoring such operational data, the programmer/tester 250 is able to monitor operation of the neurostimulation system 303, as well as the condition of the tissue in which the system is implanted.

IV. EXEMPLARY MANUAL CONTROL METHODOLOGIES

Next, with reference to FIGS. 10A and 10B, exemplary manual control mechanisms will be described that may be used with a peripheral nerve stimulation system of the type described herein. Such control mechanisms allow electrical connectivity to be selectively established between an external pulse generator 602 and a selected one of multiple target tissue locations A, B, C, D, E on nerves 512 or 513 as a function of the rotated position of a plug 721 that is removably inserted into the percuport cavity 704. FIG. 10B provides of top schematic view of that which is shown in the perspective schematic view of FIG. 10A.

Figure 10A:
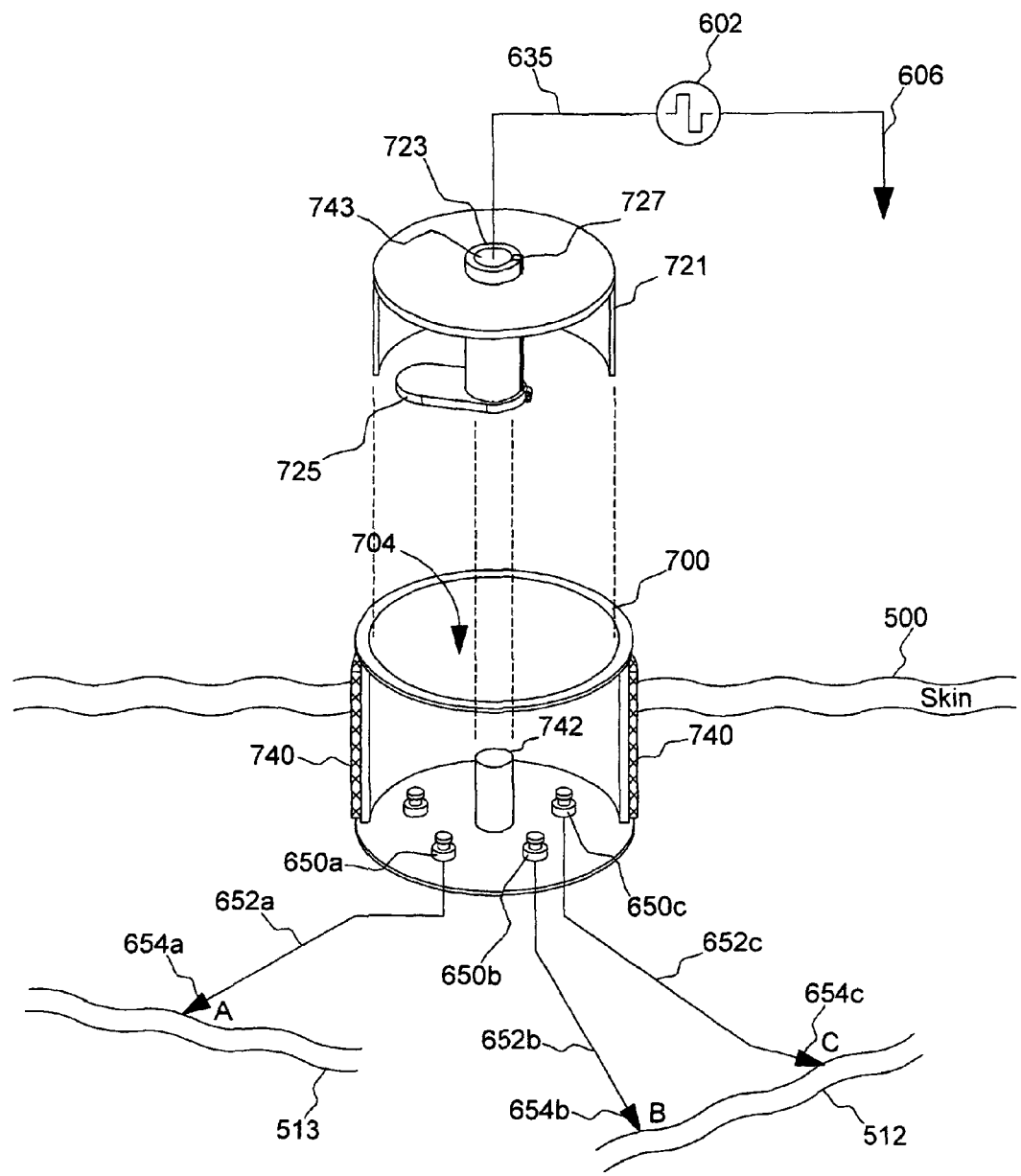
FIG. 10A schematically illustrates, in an exploded view, a peripheral nerve stimulation system employing a percuport as described herein wherein a rotatable plug (or cartridge or insert) may be removably inserted into the cavity of the percuport, and wherein the structure of the plug and percuport are such that electrical connectivity may be selectively established between an external pulse generator and a selected one of multiple target tissue locations as a function of the rotated position of the plug within the cavity, whereby the rotational position of the plug acts as a manual stimulation router.
Figure 10B:
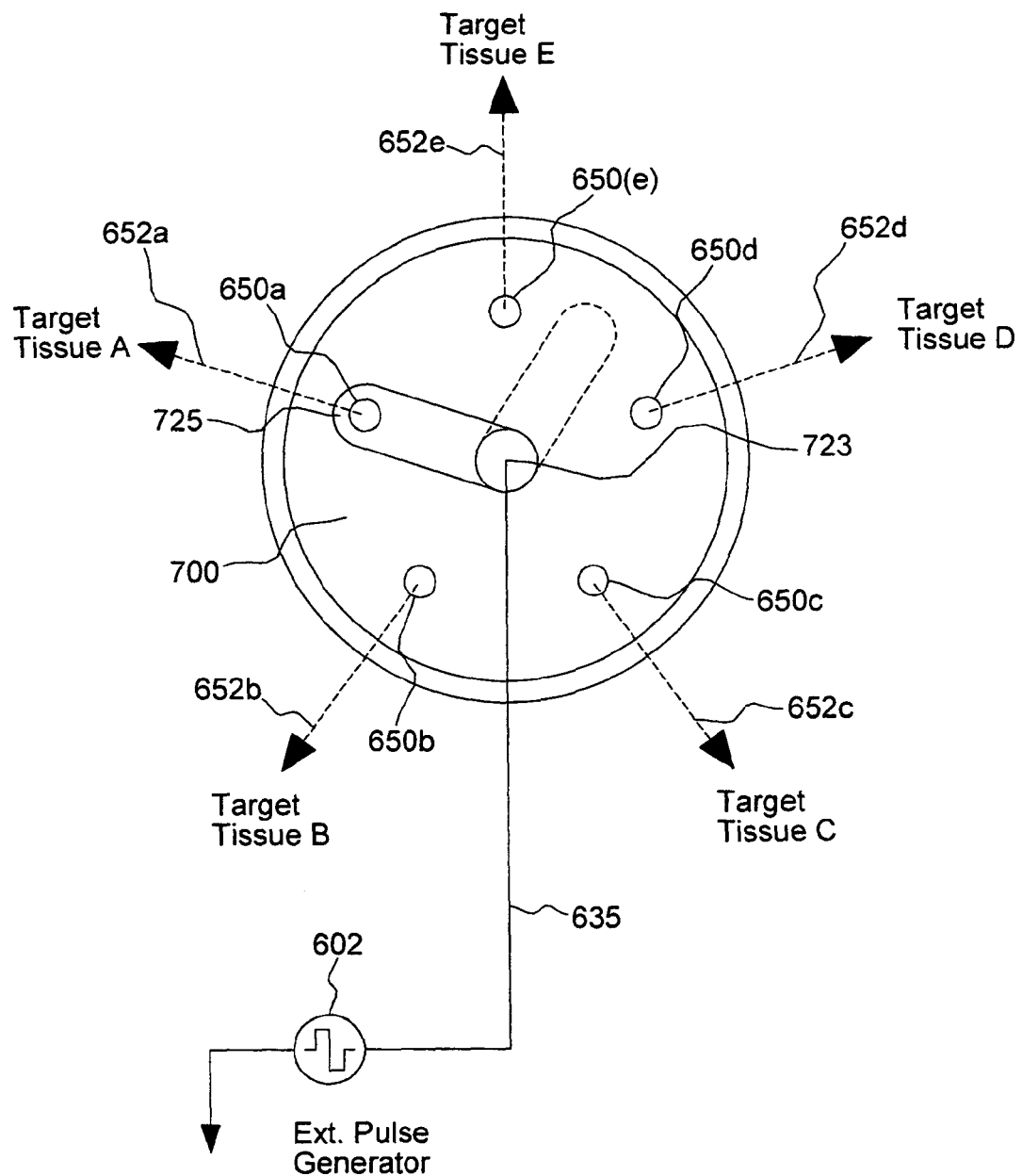
FIG. 10B illustrates in schematic fashion, as viewed from the top of the percuport, the system of FIG. 10A, and illustrates how the selection of a desired target tissue location is realized using the rotatable plug within the cavity of the percuport.

As seen in FIGS. 10A and 10B, various or multiple tissue locations may require a stimulus pulse to be delivered to them by an external pulse generator 602. Such tissue locations are identified in FIGS. 10A and 10B by the letters A, B, C, D and E. Three of these tissue locations, "A", "B" and "C" are shown in FIG. 10A as being located along nerves 513 and 512. (The other two tissue target locations, "D" and "E", are not shown in FIG. 10A, but are schematically depicted in FIG. 10B.)

In order to stimulate a desired or target tissue location, a percutaneous port 700 is embedded in the skin 500 of a patient. Leads 652a, 652b, 652c, 652d and 652e are implanted so that a distal electrode 654a, 654b, 654c, 654d and 654e on each lead is respectively positioned at or near the target tissue location "A", "B", "C", "D" or "E". The proximal end of each of these leads is then connected to the distal end of a respective feedthrough pin 650 located on the tissue side of the percuport's bottom insulative plate 702. Thus, a proximal end of lead 652a connects to the distal end of feedthrough pin 650a, a proximal end of lead 652b connects to the distal end of feedthrough pin 650b, and so on.

In order to direct a stimulus pulse from the external pulse generator 602 to the desired target tissue location, "A", "B", "C", "D" or "E", a conductive arm 725 is molded, or otherwise affixed, to a rotatable member within the plug 721. As drawn in FIG. 10A, the entire plug 721 is rotatable when inserted into the cavity 704 of the percutaneous port 700. Thus, in this instance, the conductive arm 725 may be molded into a bottom surface of the plug 721. (Other configurations could also be fashioned where only the conductive arm 725 rotates relative to the plug 721 by, e.g., twisting a knob on the top of the plug that is connected to an rotatable axle that passes through the center of the plug and is affixed to the proximal end of the conductive arm at the bottom surface of the plug.)

As drawn in FIG. 10B, a proximal end of the conductive arm 725 is located near the center of a bottom surface of the plug 721. This proximal end is electrically connected by way of a conductive trace or wire 727 that extends from the bottom surface of the plug 721 to a top surface of the plug 721 where it connects to a plug terminal 723. One of the output signal wires 635 from the pulse generator connects to this top surface plug 723. For monopolar stimulation, the other output signal wire 606 from the pulse generator 602 is grounded, e.g., by connecting it to a surface electrode located on the surface of the skin of the patient. The other end of the conductive arm extends radially outward from the center of the plug and is of a sufficient length so as to engage a proximal end of a feedthrough pin 650 when the plug 721 is inserted into the percuport cavity 704 and is rotated therein so as to cause such engagement. To facilitate rotation of the plug 721 within the cavity 704, a center post 742 may extend upward from the bottom of the percuport cavity 704, and a corresponding hole 743, adapted to receive the center post therein when the plug 721 is inserted into the cavity 704, extends upward from the bottom of the plug 721 a sufficient distance to allow the plug 721 to be fully inserted into the cavity 704.

The manner of operation of the selective stimulation mechanism illustrated in FIGS. 10A and 10B is best illustrated from the top view schematic diagram of FIG. 10B. When a stimulation pulse is to be applied to target tissue at a selected location, the plug 721 is fully inserted into the cavity 704 of the percutaneous port 700, the pulse generator is connected to the terminal 723 located on the top of the plug 721, and the plug is rotated until the distal end of the conductive arm 725 engages the proximal end of the feedthrough pin 650 that is connected through lead 652 to the desired target tissue location. For example, if target tissue location "A", located on nerve 513, is to be stimulated, the plug 721 (after being fully inserted into the percuport cavity 704 and connecting the output signal line 635 from the pulse generator 602 to the terminal 723 located on the top of plug 721) is rotated within cavity 704 until the distal end of the conductive arm 725 engages the proximal end of feedthrough pin 650a. When such engagement occurs, electrical connectivity is established between the pulse generator and target tissue location A by way of electrode 654a, lead 652a, feedthrough pin 650a, conductive arm 725, conductive trace 727, terminal 723, and wire 635. A new stimulation target site is readily selected by simply rotating the plug 721 a prescribed amount, e.g., ⅕ of a turn. A ⅕ rotation clockwise, as viewed from the top of the plug 721, would deactivate stimulation target site "A" and activate stimulation target site "E". A ⅕ rotation counter-clockwise would deactivate stimulation target site "A" and activate stimulation target site "B". A less than ⅕ rotation of the plug 721 could place the distal end of the conductive arm 725 in a location where it is not engaged with any of the feedthrough pins 650. Such positioning would effectively turn the stimulation pulses off. Thus it is seen that through selective rotation of the plug 721, while it is fully inserted into the cavity 704 of the percuport 700, any one of the stimulation sites "A", "B", "C", "D" or "E" may be selected as the site receiving a stimuli from pulse generator 602, or none of the stimulation sites may be selected, effectively disabling (turning off) the stimuli provided by the pulse generator.

The technique to manually select a desired stimulation target site, as described above (through selective rotation of the plug or cartridge inserted into the percuport's cavity 704) can also readily be achieved through electronic switching circuitry that is part of the implanted circuits 302 that form part of a neurostimulation system. The advantage of using a percuport 700 with such an implatable neurostimulation system is that it greatly facilitates the functions of powering, programming and testing such system. External batteries, battery chargers, programming circuits, and/or diagnostic equipment can be connected directly with the implanted circuits 302 of the system as needed, or desired, through the connectivity provided by the percuport. When these external elements are not needed, then nothing need be connected to the percuport. Rather, it can just have a passive plug or cover placed over it.

Next, with reference to FIGS. 11A-11F, a more robust mechanism is disclosed that allows various controls or commands to be manually generated through selective rotation of the plug 721 within the port's cavity 704. FIGS. 11A-11F are plan views showing a plurality of sensible members, e.g., conductive pads, moving relative to a pair of sensors contained within a bottom edge of a percutaneous port 700. Advantageously, being able to sense the location of the sensible members provides a manual user interface that allows a user the ability to generate control signals for controlling at least some functions of an implantable neurostimulation system through manual rotation of the plug or cartridge 721 inserted into the cavity 704 of the percutaneous port.

A neurostimulation system that utilizes a percutaneous port 700 in accordance with the present inventions may be programmed and/or controlled in any suitable manner. For example, as described briefly previously in connection with FIG. 9, some implementations of the present system may include module 228 adapted for insertion into the percuport 700, wherein module 228 may include an antenna (e.g., in combination with an FM receiver and/or BlueTooth® receiver) and receive instructions and/or programming information by way of a telemetric programmer. Some implementations of the present system may include a data connector (e.g. a micro-USB connector within the module 234 that allows instructions and/or programming information to be received by way of a wired connection to a programmer.

Alternatively, or in addition, the percutaneous port 700 and a passive selector plug 222 or 721 may be configured to function as a user interface that allows attending medical personnel and/or the patient (user of the system) to control various aspects of the operation of the system and/or to input programming commands while implanted. This is accomplished by rotating the plug 222 or 721 relative to the percuport 700 in a prescribed direction for a prescribed amount in a prescribed sequence. For such rotation to generate the needed control signals, the percuport 700 has a pattern of paired contacts, e.g., contacts 170a and 170b, and contacts 172a and 172b, placed in the bottom of the cavity 704 thereof. These contacts are arranged in a pattern as illustrated, e.g., in FIGS. 11A-11F.

More specifically, in the exemplary implementation, the pair of contacts 170a and 170b comprise a control sensor 124, and the pair of contacts 172a and 172b comprise a control sensor 126. Together, these two pairs of contacts provide a pair of circumferentially spaced control sensors 124 and 126 embedded in the bottom or floor of the percuport 700. The passive selector plug 721 (also shown as 222 in FIG. 9), functions, when inserted into the cavity 704 of the percuport 700, as a rotatable cartridge. It has a pattern of spaced metal (or conductive) surfaces, or sensible members 250, spaced around its bottom surface as shown in FIGS. 11A-11F. When the selector plug, or cartridge, 721 is inserted into the percuport 404, the conductive surface of the sensible members 250 makes electrical contact with none or both of the paired contacts of a given sensor 124 or 126. That is, the exemplary spaced sensible members 250 are electrically conductive pads. These electrically conductive pads either short together the paired contacts, or not, depending upon the rotational position of the cartridge on which the spaced sensible members 250 are placed. Thus, by monitoring the individual contacts associated with the contacts 170a and 170b (for sensor 124), and the contacts 172a and 172b (for sensor 126) with appropriate monitoring circuitry, it is possible to detect when the paired contacts 170a and 170b, or 172a and 172b, are shorted together (which occurs when the sensible member 250 is in contact with both contacts), or are not shorted together (which occurs when the sensible member 250 is not in contact with both contacts).

Thus it is seen that a detectable short occurs between contact 170a and contact 170b when these contacts are both aligned with one of the electrically conductive pads 250. Similarly, a detectable short occurs between contact 172a and contact 172b when these contacts are both aligned with one of the electrically conductive pads 250.

Such sensing advantageously may be used by the circuitry within the neural stimulator system to determine the direction and magnitude of the rotational movement of the cartridge (passive selector plug) 721 relative to the percutaneous port 700, as is discussed below with reference to FIGS. 11A-11F. The number of times there is (and is not) a short across contacts 170a/170b and contacts 172a/172b, and the order in which the short or open changes occur, is indicative of the magnitude and direction of the rotational movement of the cartridge 721 relative to the percutaneous port 700. The patient or other medical personnel may simply rotate the passive selector plug (cartridge) 721 in a predetermined manner to input commands and/or otherwise interface with the implanted circuits that form part of the neural stimulator system, as is discussed below with reference to FIG. 12.

In FIGS. 11A-11F, the exemplary sensible members 250 (which are spaced around a bottom or distal surface of the passive selector plug (or cartridge) 721 are superimposed over an end wall 702 of the cavity 704 of the percuport 700. That is, the end wall contains control sensors 124 and 126. The relative position of the control sensors 124 and 126 with respect to the superimposed sensible members 250 is shown in FIGS. 11A-11F in order to illustrate the changes in the relative rotational orientations of the sensible members and control sensors that occur when a cartridge 721 is located within the cavity 704 of the percutaneous port 700 and rotated relative thereto.

Figure 12:
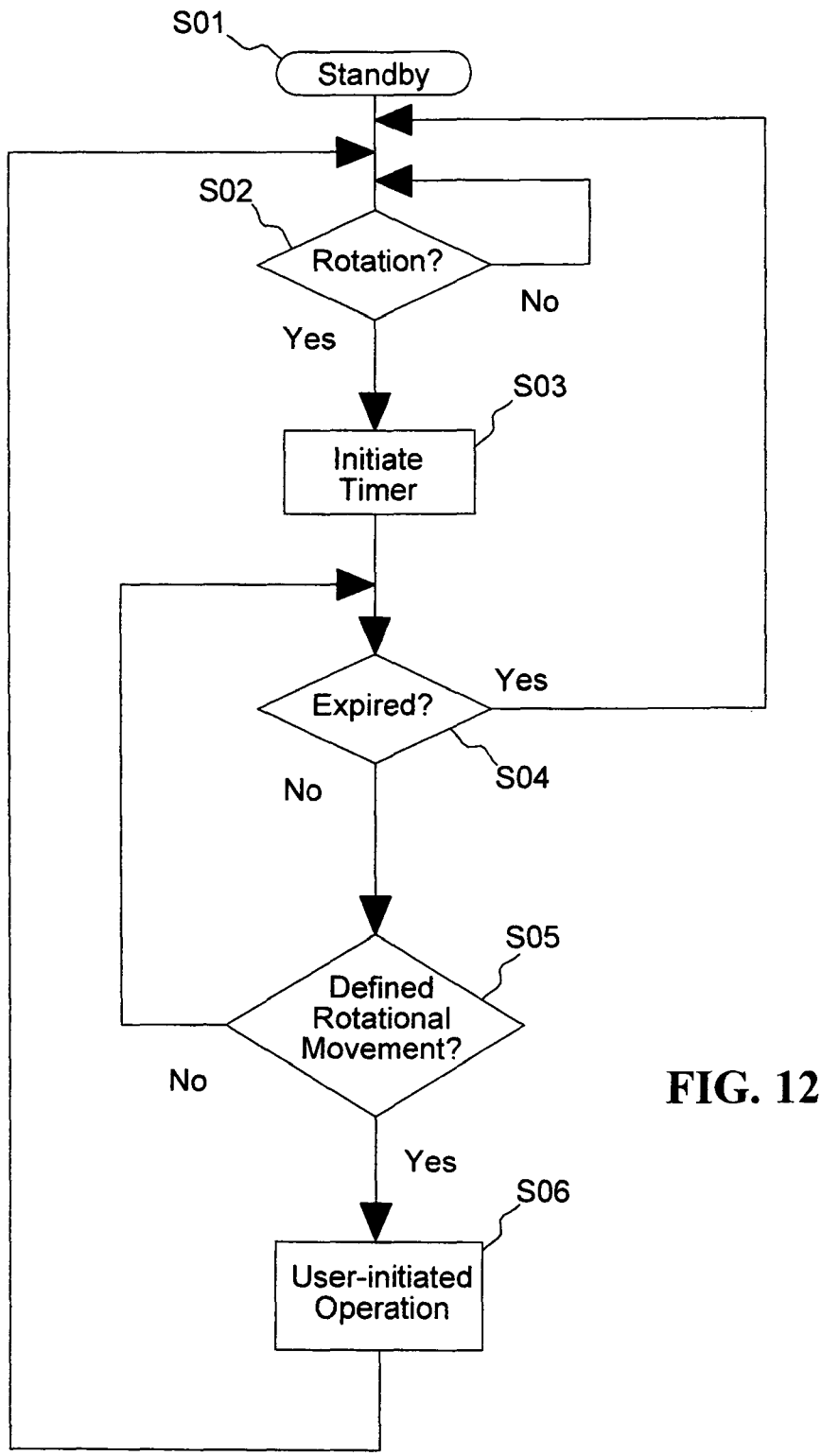
FIG. 12 is a flow chart that illustrates, in accordance with the embodiment of the invention illustrated in FIGS. 11A-11F, how rotational direction and magnitude may be detected using a rotatable cartridge (or selector plug) inserted into a percutaneous port.

FIG. 12 illustrates the manner in which the direction and magnitude of the rotational movement of the passive selector plug 721 relative to the percuport 700 may be determined. FIG. 11A represents one exemplary initial orientation of the sensible members 250 and cartridge 721 (not shown) relative to the percutaneous port 700. No sensible member 250 is aligned with the contacts on either of the control sensors 124 and 126 in the illustrated rotational orientation and, accordingly, no sensible member is sensed at either of the control sensors (a "124-no/126-no" state). Of course, and as will be clear from the discussion below, the initial rotational orientation of the sensible members 250 (and cartridge 422) need not be that shown in FIG. 11A.

In FIG. 11B, the sensible members 250 (and cartridge 721) have been rotated relative to the percutaneous port 700 in the direction of arrow A such that the sensible member 250a is aligned with the contacts 172a/172b of control sensor 126 and no sensible member is aligned with the contacts 170a/170b of control sensor 124. A sensible member will, accordingly, not be sensed at control sensor 124 and will be sensed at control sensor 126 (a "124-no/126-yes" state). The transition from the 124-no/126-no state to the 124-no/126-yes state indicates that the sensible members 250 (and cartridge 721) are moving in the counter-clockwise direction.

Turning to FIG. 11C, the sensible members 250 (and cartridge 721) have been further rotated relative to the percutaneous port 700 in the direction of arrow A such that the sensible member 250a remains aligned with the contacts 172a/172b of control sensor 126 and the sensible member 250a is now also aligned with the contacts 170a/170b of control sensor 124. A sensible member will, accordingly, be sensed at both control sensor 124 and control sensor 126 (a "124-yes/126-yes" state). The transition from the 124-no/126-yes state to the 124-yes/126-yes state, without reversion to the prior 124-no/126-no state, indicates that the cartridge 721 is continuing to move in the counter-clockwise direction without any appreciable movement in the clockwise direction.

In FIG. 11D, the sensible members 250 (and cartridge 721) have been further rotated relative to the percutaneous port 700 in the direction of arrow A such that the sensible member 250a is no longer aligned with the contacts 172a/172b of control sensor 126 and the sensible member 250a remains aligned with the contacts 170a/170b of control sensor 124. A sensible member 250 will, accordingly, be sensed at control sensor 124 and not sensed at control sensor 126 (a "124-yes/126-no" state). The transition from the 124-yes/126-yes state to the 124-yes/126-no state, without reversion to the prior 124-no/126-yes state, indicates that the cartridge is continuing to move in a counter-clockwise direction without any appreciable movement in the clockwise direction.

A subsequent transition from the 124-yes/126-no state to the 124-no/126-no state (i.e. the initial state), without reversion to the prior state, will indicate that the movement has continued in the direction of arrow A and, in the context of the illustrated implementation, that there has been a single sensor cycle and that the cartridge has rotated a total of about 60 degrees from the initial location (FIG. 11A). Continued rotation in the direction of arrow A to the location illustrated in FIG. 11E, i.e. 180 degrees from the initial location (FIG. 11A), will result in two more sensor cycles. Again, each sensor cycle is a transition from 124-no/126-no state to another 124-no/126-no state in the manner described above, and each cycle represents a rotation of 60 degrees (for the particular spaced orientation of the sensible members 250 shown in FIGS. 11A-11F).

It should be noted here that the 124-no/126-no state need not be the initial state when monitoring rotational movement of the passive selector plug 721 (or "cartridge" 721, as it is termed here for purposes of this discussion) relative to the percutaneous port 700. The initial state is merely the state present when rotational movement begins after a predetermined period without rotational movement (e.g. at least 5-10 seconds). If, for example, a sensible member 250 is aligned with the contacts on both of the control sensors 124 and 126, then the initial state will be the 124-yes/126-yes state, and a cycle will be a transition from a 124-yes/126-yes state to another 124-yes/126-yes state.

Rotational movement in the opposite direction is sensed in essentially the same way, although the yes/no transitions will occur in a different order. For example, FIGS. 11E and 11F show the rotation of the sensible members 250 (and cartridge 721) relative to the percutaneous port 700 in the direction of arrow B. The sensible member 250b will be sensed at control sensor 124 and not sensed at control sensor 126 in FIG. 11F. The transition from the 124-no/126-no state (FIG. 11E) to the 124-yes/126-no state (FIG. 11F) indicates that the cartridge is moving in a clockwise direction.

Regardless of the type of sensors and sensible members that are employed, and the manner in which the sensors and sensible members are used to identify rotational movement of the selector plug (or cartridge) 721 relative to the percutaneous port 700, the ability to identify and track such rotational movement facilitates the use of the percutaneous port and the cartridge as a user interface. By way of example, but not limitation, a variety of user-initiated implantable medical device operations may be pre-programmed into the partially implantable medical device and such operations may be actuated by the port/cartridge user interface. Each user-initiated operation may be assigned a unique defined cartridge rotational movement or a unique defined combination of rotational movements (collectively "defined cartridge rotational movement"). A time limit may be applied in at least some embodiments. For example, a defined cartridge rotational movement may be deemed ineffective unless the combination is completed within a predetermined time period (e.g. about 15 seconds from the initial detection of rotation).

The general operation of the user interface and the associated aspects of the control circuitry used to detect the relative magnitude and direction of the rotation of the selector plug 721 is graphically illustrated in the flow chart of FIG. 12. More specifically, with respect to user-initiated operation, the control circuitry of the implanted circuitry 302 will remain in a standby state (step S01) until rotational movement of the cartridge is sensed (step S02). A timer is initiated in response to the sensing of cartridge rotation (step S03). If one of the defined cartridge rotational movements is received prior to the expiration of the predetermined period (steps S04 and S05), then the user-initiated operation associated with the defined cartridge rotational movement will be initiated (step S06). If, on the other hand, one of the defined cartridge rotational movements is not received prior to the expiration of the predetermined period (steps S04 and S05), the control circuitry will return to the standby state with respect to the user interface aspects of its operation.

For example, an operation may be initiated in response to the following cartridge rotational movement: at least 360 degrees in one direction followed by rotation of at least 360 degrees in the opposite direction, with both rotations occurring within 15 seconds of the initiation of the first rotation.

Another exemplary rotation combination is rotation of at least 180 degrees in a particular direction that is completed within 15 seconds of the initiation of the rotation. The control circuitry may also be configured to actuate an audible and/or vibratory alarm (not shown) that is located within the housing 302 (FIG. 9) in response to a successful input of a defined cartridge rotational movement and/or an unsuccessful input attempt. Different versions of the alarm (e.g. one beep vs. two beeps) may be used when the alarm is actuated in response to both successful and unsuccessful attempts.

With respect to the user-initiated operations themselves, one example involves turning the system on or off. Turning the system on/off is somewhat of a misnomer because at least some circuits of the system are always on. What typically occurs when a user decides to turn his or her neural stimulator system "off" is that most of the circuits of the system are put in a sleep state, or the stimulation circuits are shut down, so that the user does not receive any stimulation until such circuits are turned "on", or placed in an "awake" state.

Another exemplary user-initiated operation is stimulation magnitude or intensity adjustment. (For a cochlear implant system, this could be termed volume adjustment.) To activate magnitude adjustment, for example, a user may rotate the cartridge 721 a prescribed amount, e.g., 60 degrees, in one direction followed within a few seconds by rotation in the other direction by the same amount. Then, once magnitude control has been activated, a clockwise rotation of the cartridge would be interpreted by appropriate control circuitry as a desire to increase the magnitude of the stimuli being applied at the target tissue location, whereas a counter-clockwise rotation of the cartridge would be interpreted as a desire to decrease the magnitude of the applied stimuli.

There are a variety of advantages associated with a user interface that is defined by the percutaneous port 700 and cartridge or plug 721 inserted therein. By way of example, and not by limitation, the present user interface obviates the need for the patient or user to possess a telemetric remote control and, accordingly, obviates the expense and potential inconvenience (if lost or otherwise unavailable) associated with a remote control. The present user interface may also eliminate the need for telemetric control for programming by the physician, or other medical personnel, thereby eliminating the need for an antenna and associated telemetric circuitry in the implanted neurostimulator system.

V. CONCLUSION

As described above, it is thus seen that the inventions described herein provide a neurostimulation system(s) wherein some components of the system are implanted and some components of the system are non-implanted, and wherein the required electrical or signal connectivity between the implanted components and non-implanted components is readily established through use of a percutaneous port embedded in the skin of a user of the system.

It is further seen that percutaneous connectivity, when implemented as described herein, provides a high degree of flexibility in how a system using such percutaneous connectivity may be configured and optimally used to best meet the needs and wants of a particular user or a particular application. That is, numerous configurations or embodiments of a percuport system allow different combinations of components of the system to be either permanently implanted or not implanted, as needed. The advantage of having some of the system components being external or non-implanted is that the non-implanted components can be readily replaced, removed upgraded, or recharged as needed.

Additionally, it is seen that the system(s) described herein, which include both implanted and non-implanted components, advantageously avoid the necessity of having to use radio frequency telemetry or inductive coupling to establish a communicative link for power and/or data signals to pass between the implanted portions of the system and the non-implanted portions of the system.

Moreover, it is seen that a preferred percutaneous port as described herein allows tissue ingrowth and vascularization. Such tissue ingrowth and vascularization advantageously provides a percutaneous seal around the periphery of the perctaneous port that functions as a very effective barrier to prevent infection.

It is also seen that the percuport-based systems described herein advantageously provide a modular-based implantable neurostimulation system wherein different component groupings or modules provide different embodiments suited for different applications or needs. Thus, one embodiment or configuration provides a system wherein most components of the system are implanted and only a few components of the system (such as a programming/testing module and recharging module) are non-implanted. On the other hand, another embodiment or configuration provides a system where most components of the system are non-implanted and only a few components of the system (such as an electrode lead) are implanted. Hence, the modularity of the systems described herein provide a full spectrum of possible embodiments—ranging from a system that is almost fully implanted to a system that is mostly non-implanted—any of which may be used to best meet the needs and demands of a particular patient group or application.

It is further seen that with the modularity provided by the percuport-based system(s) described herein, existing, approved and fully tested implantable components may be used in implantable modules or housings, and existing, approved and tested non-implantable components may similarly be used in non-implantable modules, housings or configurations. Such modularity, and use of modules containing circuits and designs that are already approved, can greatly shorten the time required to obtain regulatory approval for the implant system as a whole.

The preceding description(s) has been presented only to illustrate and describe embodiments of the invention. It is not intended to be exhaustive or to limit the invention to any precise form disclosed. Many modifications and variations are possible in light of the above teachings. Thus, while the invention(s) herein disclosed has been described by means of specific embodiments and applications thereof, numerous modifications and variations could be made thereto by those skilled in the art without departing from the scope of the invention(s) set forth in the claims.

What is claimed is:

1. A percutaneous implant system comprising:
 a percutaneous port, said percutaneous port comprising
  a bowl-like receptacle adapted to be embedded on or in the skin, including a tubular member that defines a cavity with an open end and a bottom wall formed at least in part by an insulative plate that defines a closed end, the insulative plate having an inside surface open to areas above said skin by way of said cavity and an outside surface exposed to living tissue below said skin;
  a plurality of feedthrough pins extending through said insulative plate, each feedthrough pin having a conductor that allows electrical connection to be established between a proximal end and a distal end of each feedthrough pin, the proximal end of each feedthrough pin extending above the inside surface of the insulative plate and terminating at a point adjacent to the inside surface of the insulative plate, and the distal end of each feedthrough pin extending below the outside surface of the insulative plate into said living tissue;

a mesh material disposed around a periphery of said bowl-like receptacle, said mesh material comprising a biocompatible material configured to promote tissue ingrowth and vascularization;

an external part including a plug, the plug being configured to be removably inserted into the cavity of said percutaneous port and having a plurality of conductors that are positioned to make electrical contact with the proximal ends of said feedthrough pins when said plug is inserted into said bowl-like receptacle and to electrically disconnect from said feedthrough pins when said plug is removed from said bowl-like receptacle; and an implanted part connected to the distal end of at least one of said feedthrough pins;

wherein said mesh material in combination with living tissue that grows and vascularizes therein provides a protective seal around said insulative plate for protecting against infection.

2. The percutaneous implant system as defined in claim 1 wherein when tissue has grown into the mesh material on the bowl-like receptacle the bowl-like receptacle resembles a dimple or indentation in the skin with most of the volume of the cavity residing below skin level.

3. The percutaneous implant system as defined in claim 1 wherein the plug includes a plurality of wires having a distal end terminating at the conductors within the plug, whereby the plug comprises the distal end of a connector of a cable and the plurality of wires comprise a body of the cable, and wherein a proximal end of the cable may be electrically connected to desired equipment used with the implant system for pulse generation, diagnostics, programming, or recharging purposes.

4. The percutaneous implant system as defined in claim 3 further including a plurality of implanted leads, each having a proximal end and a distal end, and an insulated conductor connecting the proximal end to the distal end;

an electrode connected to the distal end of each implanted lead;

the proximal end of each lead being connected to the distal end of one of said feedthrough pins, and the distal end of each lead with its electrode being implanted so as to be adjacent a desired target tissue location;

wherein when the proximal end of the cable is connected to an external pulse generator, and when the plug located at a distal end of the cable is inserted into the cavity of the percutaneous port, pulse stimulation is directed from the external pulse generator to a selected target tissue location through at least one of said implanted leads as a function of the relative location of the conductors embedded within the plug relative to the proximal end of the feedthrough pins.

5. The percutaneous implant system as defined in claim 4 wherein the target tissue location is manually selected through rotation of the plug within the percutaneous port.

6. The percutaneous implant system as defined in claim 1 wherein the implanted part of the percutaneous implant system includes at least a first implantable housing wherein electrical stimulation circuitry and a replenishable power source are housed, and wherein the external part of the percutaneous implant system selectively includes power circuitry for replenishing the power source housed within the first implantable housing.

7. The percutaneous implant system as defined in claim 6 wherein the external part of the percutaneous implant system further selectively includes programming circuitry for programming the electrical stimulation circuitry housed within the first implantable housing.

8. The percutaneous implant system as defined in claim 1 wherein the implanted part of the percutaneous implant system includes at least a first implantable housing wherein electrical stimulation circuitry is housed and a second implantable housing wherein a replenishable power source is housed, and wherein both the first and second housings are electrically connected to the distal ends of respective feedthrough pins of the percutaneous port, and wherein the external part of the percutaneous implant system selectively includes (a) programming circuitry for programming the operation of the electrical stimulation circuitry housed within the first implantable housing, (b) power circuitry for replenishing the power source housed within the second implantable housing or (c) diagnostic circuitry for testing the operation of the electrical stimulation circuitry.

9. In an implantable medical system comprising implanted components and external components, a percutaneous port for providing direct electrical connection between the implanted components and external components, the percutaneous port comprising:

a bowl-like receptacle configured to be embedded in the skin of a user of the implanted medical system, said bowl-like receptacle having an upper rim that defines a periphery of the receptacle, and a wall extending down from the upper rim and formed to define a single cavity adapted to receive a single removable plug and having a closed bottom inside said rim, at least a portion of said wall comprising an insulative plate;

three or more feedthrough pins extending through the insulative plate into said single cavity, each feedthrough pin having a proximal end and a distal end and an electrical conductive body that connects the proximal end and the distal end, the proximal end comprising the end of the feedthrough pin accessible from the inside of the cavity of the percutaneous port, and the distal end comprising the end of the feedthrough pin accessible from the outside of the cavity of the percutaneous port;

a mesh material disposed around a periphery of said upper rim, said mesh material comprising a biocompatible material configured to promote tissue ingrowth and vascularization;

wherein said percutaneous port is configured to be embedded in the skin of a user so that the upper rim of the percutaneous port is even with, or extends slightly above, a surface of the skin, and so that the volume of the cavity defined by the walls of said percutaneous port lies largely below skin level so as to form a dimple or indentation in the skin;

wherein the wall of said percutaneous port protects tissue under the skin from exposure and infection; and wherein the mesh material provides a location where living tissue can grow into the mesh material and provide a barrier around the periphery of the percutaneous port that protects the tissue from infection; and further wherein direct electrical connection may be established between external components of the implanted medical system and implanted components of the implanted medical system through said feedthrough pins passing through the wall of said percutaneous port.

\* \* \* \* \*